(12) United States Patent
Avetisov et al.

(10) Patent No.: US 12,173,697 B2
(45) Date of Patent: Dec. 24, 2024

(54) HARVESTING OF THERMAL ENERGY BY NANOMACHINES

(71) Applicant: MOLECULAR MACHINES CORPORATION LTD., Tel Aviv (IL)

(72) Inventors: Vladik Avetisov, Moscow (RU); Roman Iliev, Moscow (RU)

(73) Assignee: MOLECULAR MACHINES CORPORATION LTD., Tel Aviv (IL)

(*) Notice: Subject to any disclaimer, the term of this patent is extended or adjusted under 35 U.S.C. 154(b) by 14 days.

(21) Appl. No.: 18/268,237

(22) PCT Filed: Dec. 17, 2021

(86) PCT No.: PCT/IB2021/061977
§ 371 (c)(1),
(2) Date: Jun. 18, 2023

(87) PCT Pub. No.: WO2022/130345
PCT Pub. Date: Jun. 23, 2022

(65) Prior Publication Data
US 2024/0060478 A1 Feb. 22, 2024

Related U.S. Application Data

(60) Provisional application No. 63/127,367, filed on Dec. 18, 2020.

(51) Int. Cl.
*F03G 7/00* (2006.01)
*B82Y 15/00* (2011.01)

(52) U.S. Cl.
CPC .............. *F03G 7/017* (2021.08); *B82Y 15/00* (2013.01); *F03G 7/008* (2021.08); *F03G 7/0252* (2021.08)

(58) Field of Classification Search
CPC ................................................. F03G 7/00–135
See application file for complete search history.

(56) References Cited

U.S. PATENT DOCUMENTS

| 10,224,835 B1 | 3/2019 | Singh | |
| 2022/0151916 A1* | 5/2022 | Avetisov | .............. A61K 9/0009 |

(Continued)

FOREIGN PATENT DOCUMENTS

| EP | 3386090 A1 * | 10/2018 | ............. B82B 1/003 |
| WO | 2018106998 A1 | 6/2018 | |

(Continued)

OTHER PUBLICATIONS

Oligomeric "Catastrophe Machines" with Thermally Activated Bistability and Stochastic Resonance Vladik A. Avetisov, Anastasia A. Markina, and Alexander F. Valov The Journal of Physical Chemistry Letters 2019 10 (17), 5189-5192 DOI: 10.1021/acs.jpclett.9b01261 (Year: 2019).*

(Continued)

*Primary Examiner* — Laert Dounis
(74) *Attorney, Agent, or Firm* — The Roy Gross Law Firm, LLC; Roy Gross

(57) ABSTRACT

Disclosed are oligomeric machines for energy harvesting having a first oligomeric module having a first end and a second end, a second oligomeric module having a first end and a second end, and at least one electric generating element. Exemplary oligomeric machines are configured to exhibits stochastic resonance and/or spontaneous vibrations and are configured such that in response to a prescribed amount of energy applied thereto, relative movement occurs between the first oligomeric module and the second oligomeric module in a manner causing the mechanical action of the second oligomeric module on the electric generating element to produce an electrical voltage and/or current.

16 Claims, 18 Drawing Sheets

(56) References Cited

U.S. PATENT DOCUMENTS

| | | | |
|---|---|---|---|
| 2023/0024235 A1* | 1/2023 | Avetisov | B82B 1/002 |
| 2024/0060478 A1* | 2/2024 | Avetisov | F03G 7/0252 |
| 2024/0247645 A1* | 7/2024 | Avetisov | B82Y 15/00 |

FOREIGN PATENT DOCUMENTS

| | | | | |
|---|---|---|---|---|
| WO | WO-2020194066 A2 * | 10/2020 | | A61K 47/32 |
| WO | WO-2021123915 A1 * | 6/2021 | | B82B 1/002 |
| WO | WO-2023053010 A1 * | 4/2023 | | |

OTHER PUBLICATIONS

Markina A, Muratov A, Petrovskyy V, Avetisov V. Detection of Single Molecules Using Stochastic Resonance of Bistable Oligomers. Nanomaterials. 2020; 10(12):2519. https://doi.org/10.3390/nano10122519 (Year: 2020).*

Avetisov, Vladik A., Anastasia A. Markina, and Alexander F. Valov. "Catastrophe machines a few nanometers in size." arXiv preprint arXiv:1811.10384 (2018). (Year: 2018).*

* cited by examiner

2600  
WEEKLY-FLUCTUATING  
OPEN SHAPE  
BELOW LSTC

280K

2601  
WEEKLY-FLUCTUATING  
CLOSED SHAPE  
ABOVE LSTC

310K

2602  
STRONGLY-FLUCTUATING  
SEMI-OPEN SHAPE  
ABOVE LSTC

330K

2700  
UNFOLDED ROD-LIKE  
SHAPE  
BELOW LCST

290K

2701  
FOLDED LEVER-  
SHAPE FORM  
ABOVE LCST

310K

HARVESTING OF THERMAL ENERGY BY NANOMACHINES

CROSS-REFERENCE

This application is a National Phase of PCT Application No. PCT/IB2021/06197 having International filing date of Dec. 17, 2021, which claims the benefit of priority of U.S. Provisional Application No. 63/127,367, filed Dec. 18, 2020, entitled "HARVESTING OF THERMAL ENERGY BY NANOMACHINES"; the contents of which are all incorporated herein by reference in their entirety.

FIELD

This application is directed towards nanomechanical devices whose functioning is related to bistability of nanoscale oligomeric structures and/or their nanoscale compositions.

BACKGROUND

Industrial miniaturization of devices and machines is typically carried out by top-down design. The creation of smaller and smaller components and devices is desired, and manufacturing is moving to the nanometer scale from the micrometer scale. Approaching the size of about 10 nm by top-down design, the cost of precise manipulations using macroscopic devices typically increases and may become prohibitively expensive. Alternatively, bottom-up strategies which design functional devices on the nanometer scale from building elements of sub-nanometer (atomic) size may prove beneficial.

SUMMARY

In some embodiments, molecular and/or oligomeric machines comprising oligomeric modules are selected and joined so as to exhibit conformational bistability wherein a relative orientation between oligomeric modules may change from a first orientation to a second orientation in response to one or more stimuli.

In some embodiments, an oligomeric machine comprises a synthetic material including a first oligomeric module and a second oligomeric module joined to the first oligomeric module to form an oligomeric chain, at least one bending or hinge location at a position of co-joinder between the first oligomeric module and the second oligomeric module, the bending or hinge location permitting relative flexure between the first oligomeric module and the second oligomeric module, at least one electric generating element, a substrate configured relative to the at least one electric generating element and the oligomeric chain such that the relative flexure between the first oligomeric module and the second oligomeric module results in mechanical interaction between at least the second oligomeric module of the oligomeric chain and the at least one electric generating element, and wherein the oligomeric chain is formed such that in response to a stimulus, the relative flexure occurs between the first oligomeric module and the second oligomeric module in a manner causing the mechanical interaction between the second oligomeric module and the electric generating element, and wherein the mechanical interaction produces a change in electrical voltage associated with the at least one electric generating element.

In some embodiments, an oligomeric machine comprises a synthetic material including a first oligomeric module and a second oligomeric module joined to the first oligomeric module to form an oligomeric chain, at least one bending or hinge location at a position of co-joinder between the first oligomeric module and the second oligomeric module, the bending or hinge location permitting relative flexure between the first oligomeric module and the second oligomeric module, at least one piston element, a substrate configured relative to the at least one piston element and the oligomeric chain such that the relative flexure between the first oligomeric module and the second oligomeric module results in mechanical interaction between at least the second oligomeric module of the oligomeric chain and the at least one piston element, and wherein the oligomeric chain is formed such that in response to a prescribed amount of energy applied thereto, the relative flexure occurs between the first oligomeric module and the second oligomeric module in a manner causing the mechanical interaction between the second oligomeric module and the piston element, and wherein the mechanical interaction produces a mechanical force.

BRIEF DESCRIPTION OF DRAWING(S)

FIG. 1 illustrates two conformational states of oligo-NIPAm-20a.

DETAILED DESCRIPTION

Figure 1:
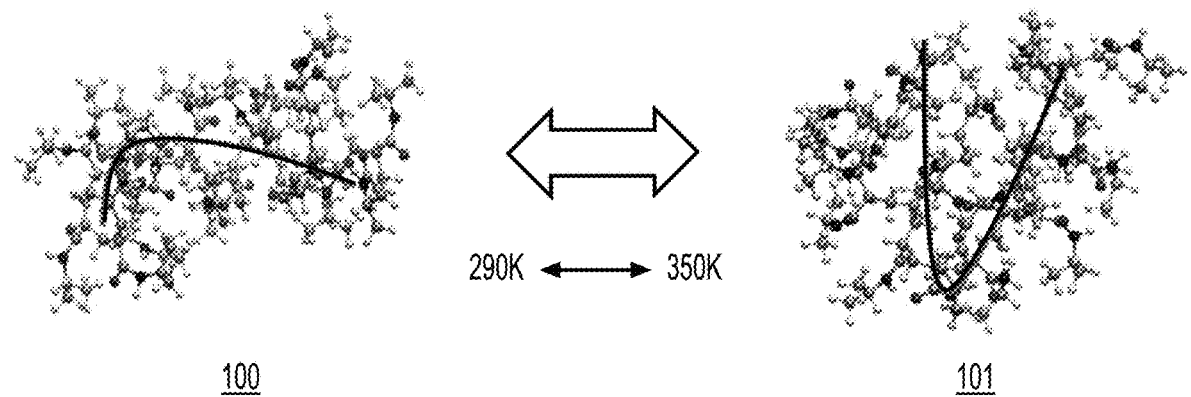

Humans have been using wind power since the inventions of the sail and the wind turbine. However, it is not always windy. A windmill in an office to grind coffee beans is not a good idea. Yet, even with complete calm, molecules in the air fly as fast as if there was a hurricane. There are always energetically rich fluctuations in a gas, which might be useful by manipulating a two-state system. A two-state dynamical system can work as a nano-windmill.

Because it averages all fluctuations, classical thermodynamics does not match well with nanomachines. In contrast, when designing the nanomachines, random perturbations should be explicitly considered. Fortunately, stochastic thermodynamics has made breakthrough progress over the past 20 years. Today, stochastic thermodynamics is the same background for nanomachines as classical thermodynamics is for ordinary engines. Also, the powerful methods of full-atomic simulations of complex molecular systems and the impressive tools for single-molecule manipulating have emerged. In fact, modern nanosciences and nanotechnologies are leading to nanomachines.

From the viewpoint of stochastic thermodynamics, a nanometer-sized molecule may have a specific dynamic to work like a machine. A nanometer-sized molecule has thousands of atoms and thousands of degrees of freedom. However, machine-like action implies low-dimensional dynamics, which are supposed to be realized through collective atomic motions associated with a few slowest degrees of freedom. Thus, to perform machine-like action, the slowest degrees of freedom may be dynamically separated from all faster degrees of freedom. For example, a two-state system may imply an abrupt state change when some stimulus crosses a threshold value. Such action is associated with the behavior of a nonlinear dynamical system. For example, consider an elastic rod. Indeed, the rod remains straight under light longitudinal compression. However, as soon as the compression exceeds a critical level, the straightened state becomes unstable, and the rod bends up or down. Above critical compression, the rod behaves like a two-state machine. It can perform mechanical work via jumping from one state to another when applying a lateral force. However, at the molecular scale, the rod can jump itself. If random perturbations can activate transitions between the two states, the rod will jump spontaneously, performing spontaneous vibrations. Random jumping can be transformed into regular jumps by weak oscillating compression. This phenomenon may be called stochastic resonance.

Spontaneous vibrations and stochastic resonance are attractive for using thermal-bath energy as a "fuel" for nanomachines. For micron- or even submicron-sized systems, the thermal fluctuations may be too weak to activate spontaneous vibrations: much stronger perturbations may be needed. Thermal fluctuations can perturb systems of just a few nanometers in size. Therefore, if a nanometer-sized molecule is bistable and the bistability barrier is comparable to the thermal fluctuations energy, the spontaneous vibrations will appear naturally. Such energy harvesting may be accomplished using any of the materials described herein, or using combinations of such materials.

Oligomeric and/or molecular machines may include devices capable of exhibiting controlled movements at the nanoscale. Some oligomeric and/or molecular machines exhibit conformational bistability wherein these machines, under certain conditions, may be capable of changing between at least two conformations upon application of one or more stimuli. Some oligomeric and/or molecular machines may comprise various components such as oligomeric modules, bending and/or hinge regions, and extenders.

Oligomeric machines may be configured to exhibit conformational bistability and may comprise oligomeric modules selected and joined so as to exhibit controllable and/or reproducible conformational changes. Conformational bistability may be characterized by the existence of at least two distinguishable conformational states wherein spontaneous or reproducible transitions between such states may be controllable. Non-limiting examples of conformational states include spatial shape or arrangement of a molecular, oligomeric, and/or polymeric material. For example, an oligomeric chain may have a stretched shape or it may be folded into a bent shape. Bistability implies that at least two conformational states are sufficiently stable or metastable for a desired process or application. For example, an oligomeric chain with a stretched state and a bent state may be repeatedly transitioned back-and-forth between the stretched state and bent state by, for example, subjecting the oligomeric chain to a temperature in a critical temperature range or/and to a force load in a critical force range. Oligomeric machines exhibiting conformational bistability may be utilized for nanomechanical operations. Nanomechanics refers to the movements performed by material structures such as, for example, molecular, oligomeric, and/or polymeric structures on the nanometer scale. The atomic fluctuations of such structures are typically much smaller than the structure size and its movements. Currently, industrial miniaturization of devices and machines is carried out on the basis of top-down design. At the present, the scale of several tens of nanometers is industrially achievable. At the same time, it becomes clear that approaching the size of about 10 nm by top-down design, the cost of precise manipulations using "macroscopic" devices sharply increases and becomes too expensive in typical batch production. Alternatively, the manipulations by objects of a few nanometers in size should utilize "molecular machines" of approximately the same size. Nanomechanics enables machine-like movements at the nanometer scale using rigid nanoscale materials. Machine-like movement may imply the motion of a "solid" unit, i.e. the movements of rigid structures, wherein atomic fluctuations are much less than the structure's characteristic sizes and the scale of their movements. Since the atomic fluctuations at room temperature are of the order of 1 Angstrom, the minimal size of functional units will generally not be significantly less than 1 nanometer.

Stochastic resonance is a particular dynamic mode that may be realized by applying a periodic stimulus to spontaneously vibrating bistable system. Spontaneous vibrations are a particular dynamic mode that may be characteristic of bistable system. Bistability may be realized by nonlinear dynamical systems with critical behavior. A critical temperature or critical force relates to the critical point where a new (second) branch of steady states dynamics appears and the system becomes bistable.

Figure 2:
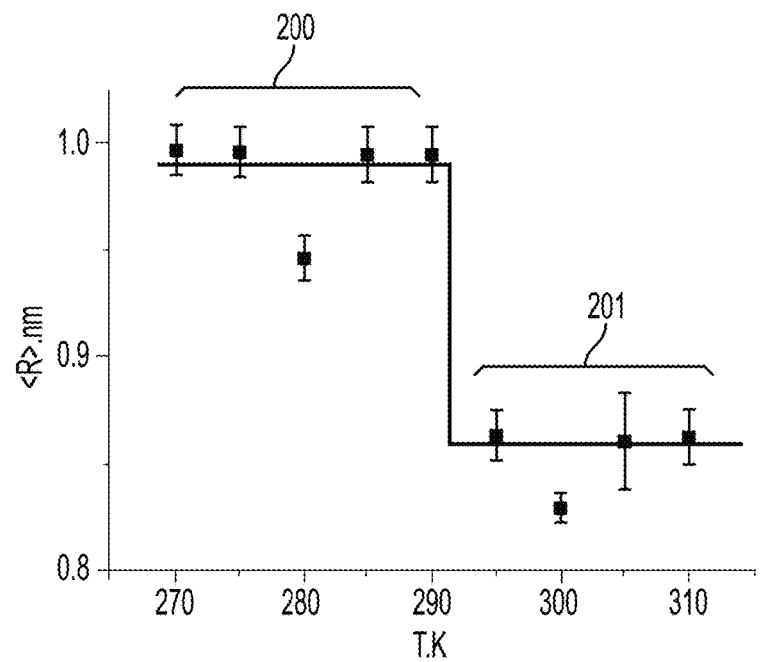
FIG. 2 illustrates the radius of gyration vs. temperature of an exemplary oligo-NIPAm-20 embodiment.
Figure 3:
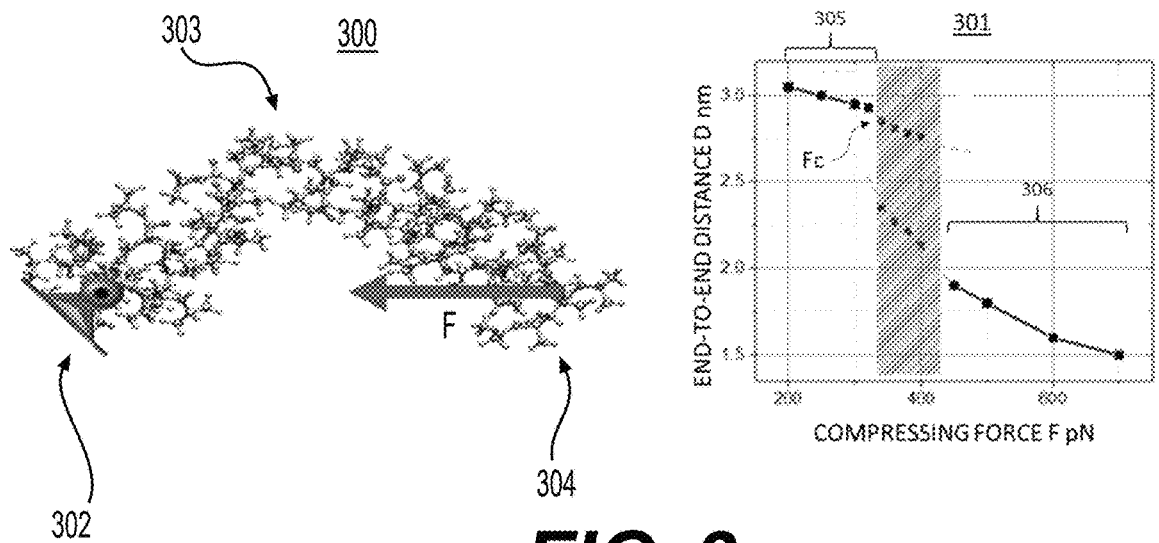
FIG. 3 illustrates end-to-end distance d vs. compressing force F wherein Fc is the critical compression for an exemplary oligo-NIPMAm-30 embodiment.

FIG. 1 illustrates an exemplary embodiment comprising two distinguishable conformational states of poly-N-isopropylacrylamide of 20 units in length (oligo-NIPAm-20) with temperature-controlled transitions between an open (100) and a closed (101) conformational state. FIG. 2 illustrates a temperature-controlled transition between an open (200) and a closed (201) state of an exemplary oligo-NIPAm-20 at 290 K. FIG. 3 illustrates control of conformational transitions in an exemplary embodiment comprising oligo-NIPMAm-30 (element 303) wherein compressive forces (304) are applied to the ends of the oligo-NIPMAm-30 with one end fixed (302). Critical forces may be related to critical temperatures for the bistability of oligomeric machines. In this exemplary embodiment, under compression close to 400 pN (pico-Newton) an oligomeric machine becomes bistable, that is, a new branch of steady states with close conformations (306) appears, and the system can spontaneously vibrate (301) between the open conformational state (305) becomes unstable and the oligomer sharply transits to the closed conformational state (306).

Figure 4:
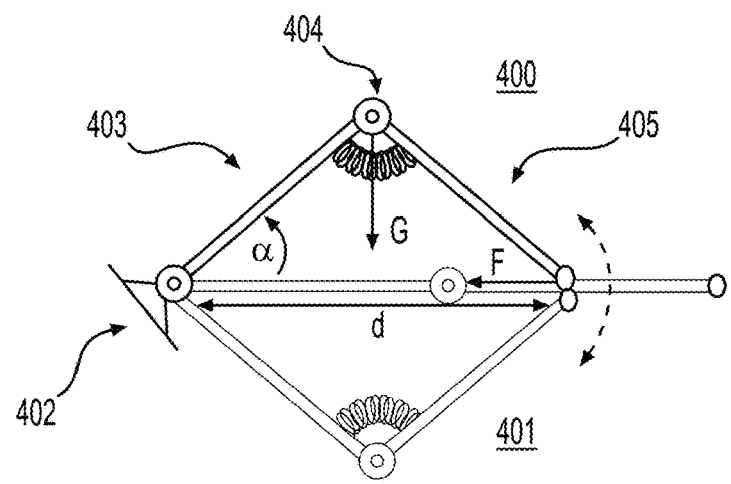
FIG. 4 illustrates an Euler arch associated with certain aspects of presently disclosed embodiments.
Figure 5:
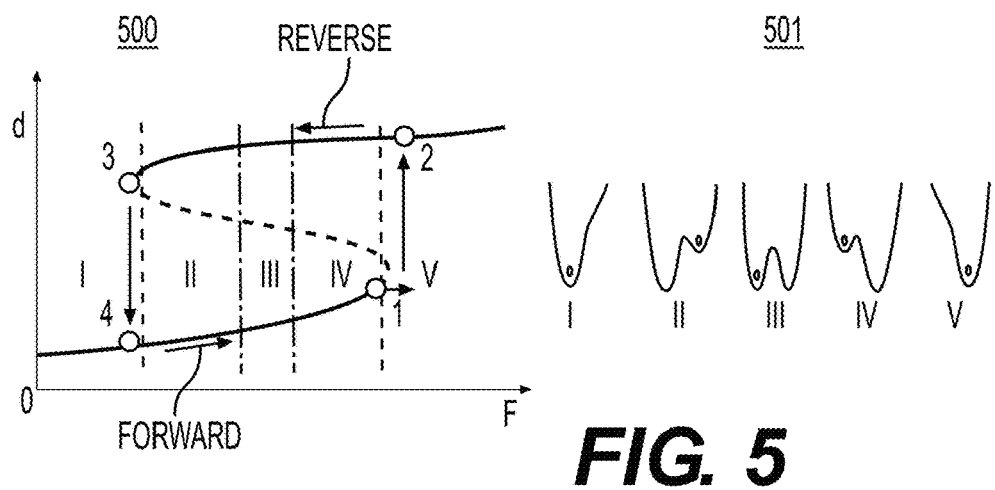
FIG. 5 illustrates a bifurcation diagram of a cusp catastrophe model represented by distances d between the edges of the Euler arch vs pulling force F.
Figure 6:
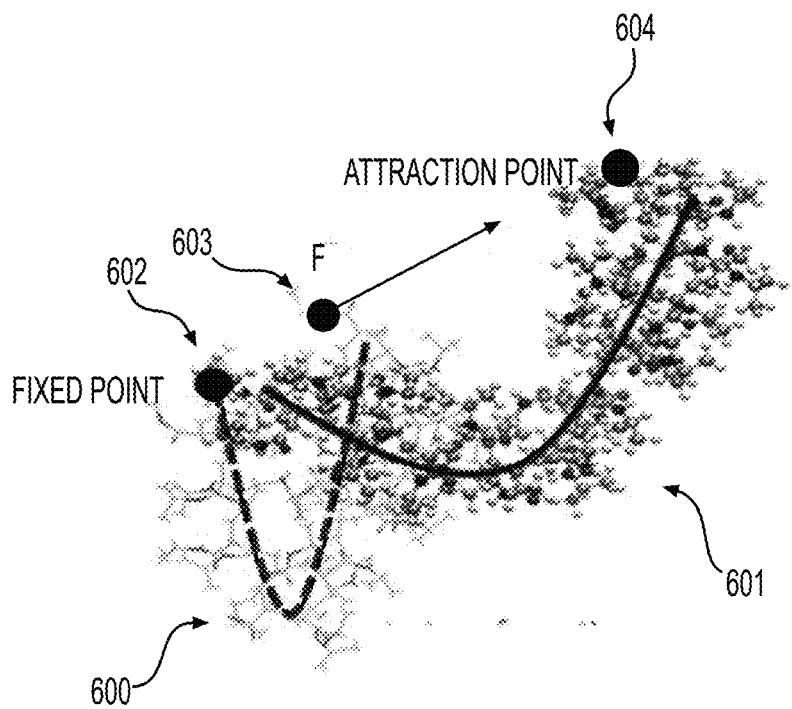
FIG. 6 illustrates an exemplary embodiment with a simulated applied force where one edge of a bent oligomeric chain is fixed, and a force F is applied to another edge of the chain.
Figure 7:
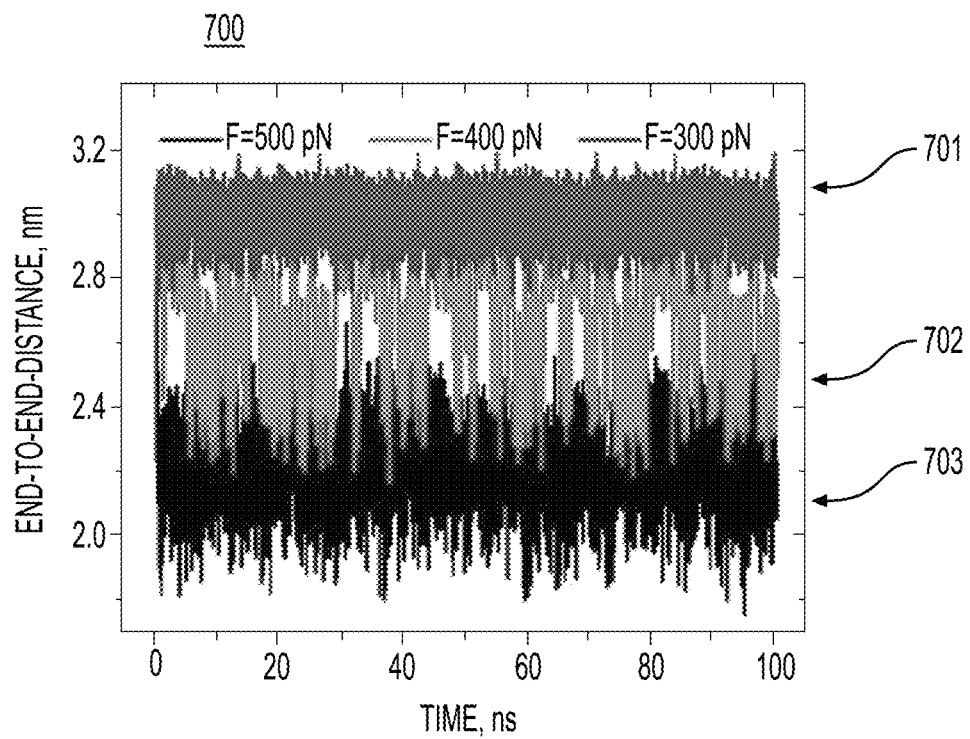
FIG. 7 depicts end-to-end distance vs. time for an exemplary NIPMAm-30 oligomer.
Figure 8:
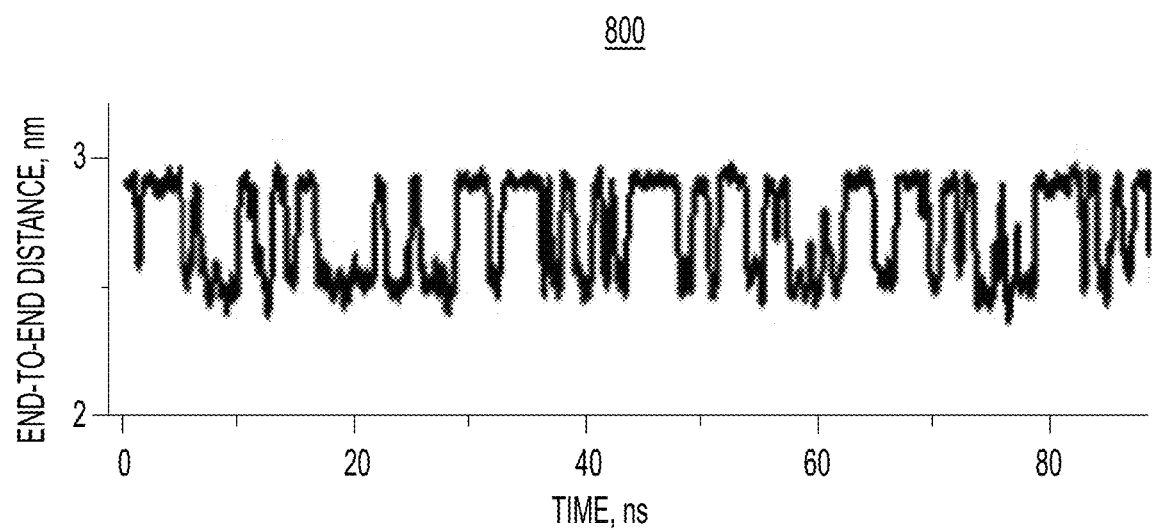
FIG. 8 depicts spontaneous vibrations of an exemplary embodiment oligo-NIPMAm-30 (top panel) and statistical weights for visits of the "open" and "close" states when the pulling force F passes through a critical value.
Figure 8:
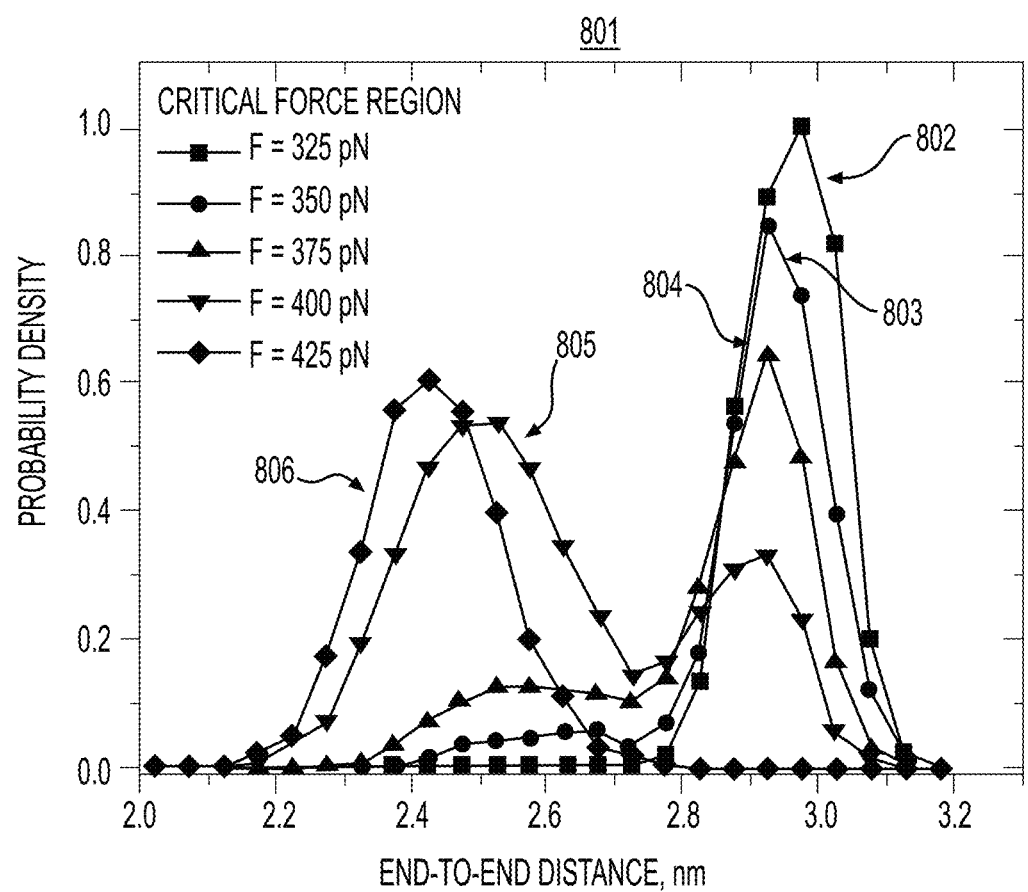

In some embodiments, mechanical properties may be similar to the action of classical nonlinear mechanical systems such as an Euler arch or Zeeman's catastrophe machine. Catastrophe machines are mechanical devices with dynamics that demonstrate the "catastrophes". FIG. 4 depicts an Euler arch which is one of the simplest mechanical constructions with "catastrophic" behavior and consists of two rigid rods (403 and 405) joined by an elastic hinge (404). To demonstrate the "catastrophes", one edge of an Euler arch is fixed (402) and another edge is compressed by an external force. As the compressing force reaches a critical value, the Euler arch abruptly bends. When the compressing force increases, the Euler arch shows bistability with jump-like transitions from a stretched state into a bent state (400 and 401 depict two different bent states). For small compressing forces, the Euler arch remains stretched, however, as soon as the compressing force passes the critical value, the Euler arch is abruptly bent. In the theory of dynamical systems, such sharp changes are known as "catastrophes". Accordingly, the Euler arch is referred as a "catastrophe machine". The same catastrophes can be demonstrated by applying a pulling force to the bent arch. The bistability of an Euler arch is described by a bifurcation diagram of the cusp catastrophe model as depicted by FIG. 5. In regions I and V of FIG. 5, the potential energy has a single minimum related to the bent and straightened Euler arch, respectively. In the regions II and IV, there are two energy minima, among which one of them dominates, while in the region III two local energy minima are symmetric and neither of the two states dominates. The region III is the bistability region where the arch subjected to random perturbations may spontaneously vibrate between two bent states. The spontaneous vibrations may be transformed into regular jumps between two states, called stochastic resonance, by applying a weak harmonic force. Some exemplary embodiments comprise nanoscale oligomeric machines configured to exhibit "catastrophic" mechanical behavior. with bistability, spontaneous vibrations and stochastic resonance. A preferred embodiment nanomechanical device that acts as a catastrophe machine may be an oligomeric machine consisting of two persistent Kuhn segments joint by a bending or hinge location. Such embodiments surprisingly demonstrate dynamic behavior of oligomeric machines of a few nanometers in size. This may be demonstrated by two exemplary oligomeric machines (oligo-NIPAm-20 oligo-NIPMAm-30) subjected to the action of a pulling force studied by computer simulation methods. GROMACS molecular dynamics package were used to perform atomistic simulations of the dynamics of oligomeric machines in water at temperatures below and above the critical temperature of transition from the bent state to the stretched state. OPLS-AA force field in combination with TIP3P explicit water model are used to describe inter- and intra-molecular interactions. In such exemplary embodiments, an oligomeric machine in the bent (folded) conformation (600) at constant temperature is subjected to an applied force at one edge of the chain (603) and another edge of the chain was fixed (602) induce a transition into the straightened (unfolded) conformation (601). This configuration is depicted in FIG. 6. Varying the pulling force, F, that initiates the transition from the bent state to the straightened state, the threshold force is found to be about 400 pN for a NIPMAm-30 oligomer, and 120 pN for an oligo-NIPAm-20 oligomer. In FIG. 7, time series of edge-to-edge distance of a NIPMAm-30 oligomer are shown. Curve (701) correspond to the pulling force less than the threshold value, curve (702) correspond to the critical force region, and curve (703) correspond to the pulling force greater than the threshold value. The pulling forces less than the threshold value do not stimulate the transition from the bent conformations to the stretched conformations. The forces sufficiently greater than the threshold value stimulate a jump-like transition from the bent conformation to the stretched conformation for rather short time. The pulling forces in the critical region stimulate spontaneous vibrations between the bent conformations and the stretched conformations. The dynamics of the compositions exhibit conformational bistability when the external force passes the threshold value. FIG. 8 demonstrates conformational bistability for some exemplary embodiments. In FIG. 8, curve (802) corresponds to a force of 325 pN, curve (803) corresponds to a force of 350 pN, curve (804) corresponds to a force of 375 pN, curve (805) corresponds to a force of 400 pN, and curve (806) corresponds to a force of 425 pN. In these exemplary systems near a threshold force, oligo-NIPMAm-30 and oligo NIPAm-20 alternately visit the bent and stretched states. Panel (800) depicts spontaneous vibrations in the critical force region. Conformational bistability with spontaneous vibrations is demonstrated for small deviations, up to 20 pN, around 390 pN for oligo-NIPMAm-30 and 120 pN for oligo-NIPAm-20. For larger deviations, the oligomeric machines have a well defied state, bent or stretched, respectively. Thus, bistability may be demonstrated by the dynamics exemplary embodiments. In this sense, oligo NIPMAm-30 and oligo-NIPAm-20 may be configured to exhibit "catastrophic" nanomechanical dynamics.

Figure 9:
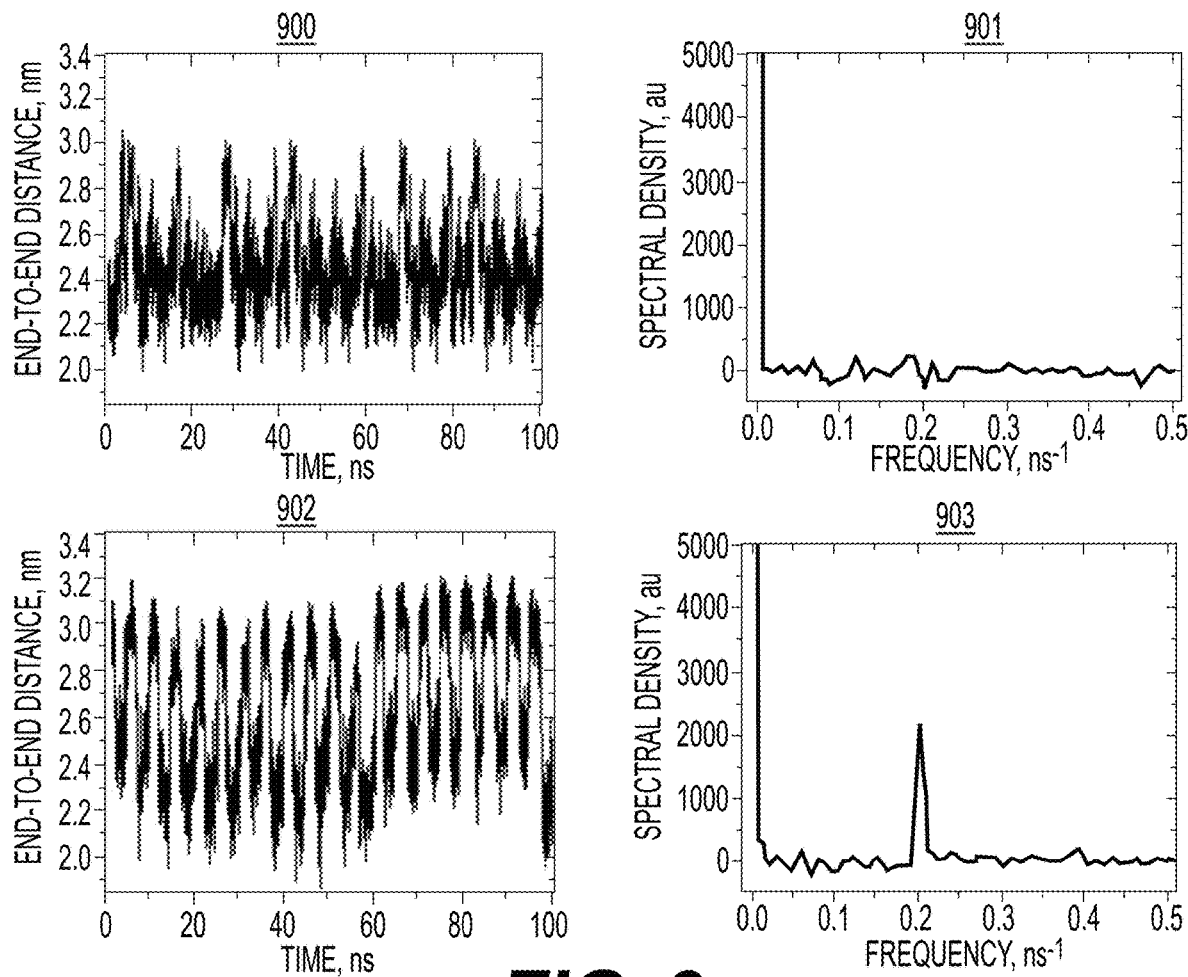
FIG. 9 depicts stochastic resonance of an exemplary NIPMAm-30 oligomer controlled by a weak oscillating force.
Figure 10:
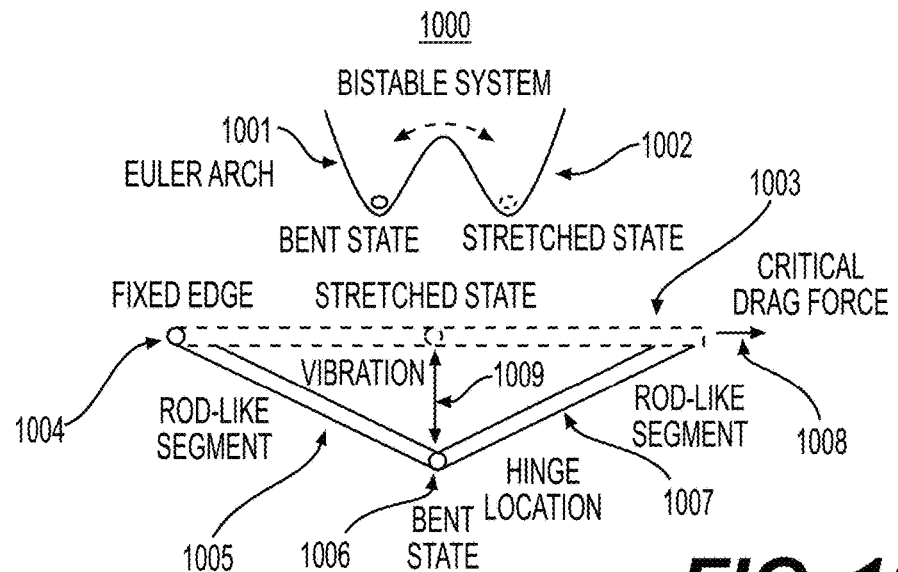
FIG. 10 depicts a bistable system capable of spontaneously vibrating between two conformations.
Figure 11:
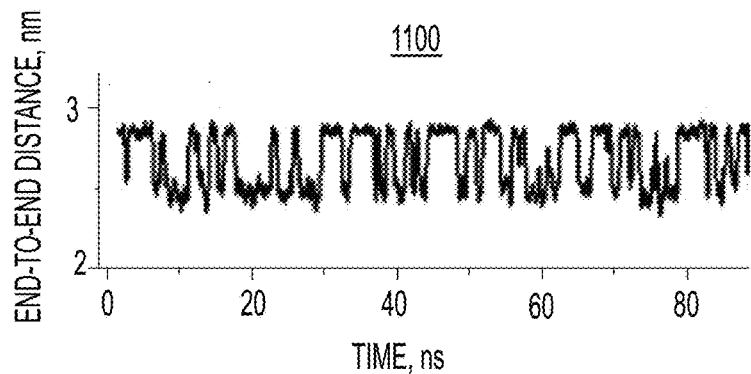
FIG. 11 depicts time dependence of the end-to-end distances in an exemplary oligo-NIPMAm-30 embodiment in a vibratory regime near a critical pulling force.
Figure 12:
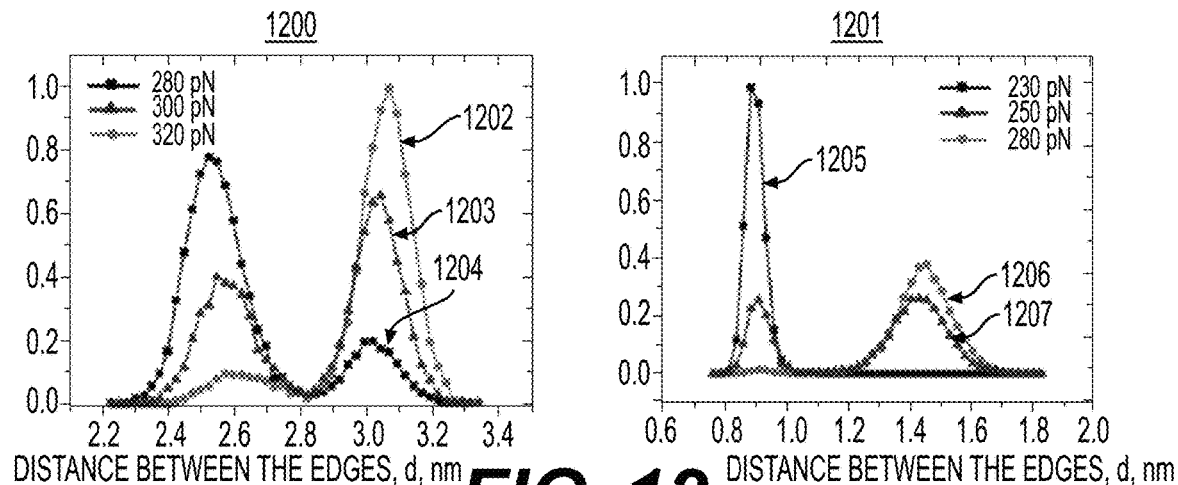
FIG. 12 depicts statistics of bent and stretched states normalized on the maximum value for an exemplary oligo-NIPMAm-30 embodiment near (left) and far from (right) a critical pulling force.
Figure 13:
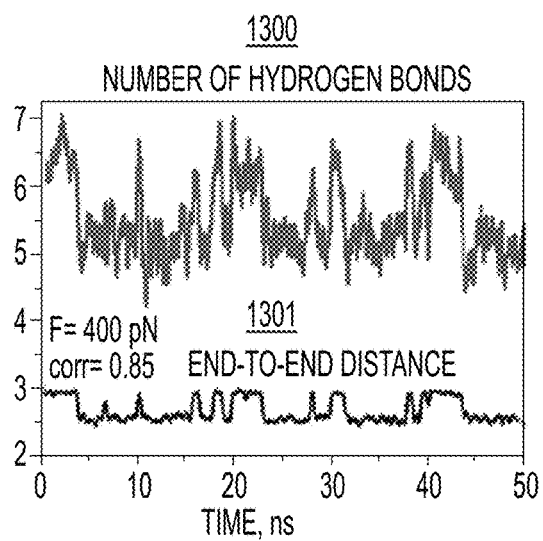
FIG. 13 depicts time dependence for the number of hydrogen bonds surrounding a hinge location of an exemplary NIPMAm-30 embodiment and end-to-end distance of the chain for pulling forces Fc=400 pN (left panel) and F=500 pN (right panel).
Figure 13:
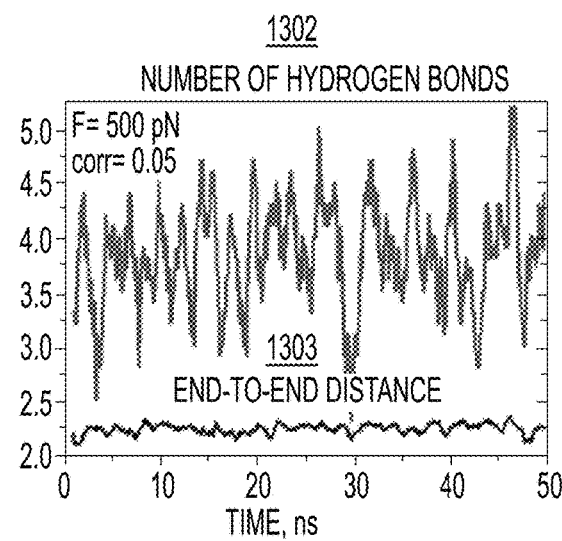

In some embodiments, cyclic variation of a control parameter near a threshold value may be demonstrated using full atomic computer simulations in a stochastic resonance regime by applying an additional weak oscillating force to simulate stochastic resonance. The cyclic variation of the pulling force near a threshold value Fc=400 pN was realized by setting an elementary charge at the movable end of the oligomer and applying a weak oscillating electrical field with the amplitude $E_0$ ranged from 0.01-1.00 V/nm and the frequency varied from 50-500 MHz. Stochastic resonance was unambiguously observed under variation of these controlling parameters. An exemplary embodiment is illustrated in FIG. 9 wherein stochastic resonance of a NIPMAm-30 oligomer controlled by a weak oscillating force is depicted. Plots (900) and (901) show spontaneous vibrations between two states and the frequency spectra of the transitions in the case when the oscillation force is not applied to the oligomer. Plots (902) and (903) show a stochastic resonance effect and the frequency spectra of the transitions in the case when a weak oscillation force controls the oligomer vibrations. In some embodiments, the nanometer scale makes it possible to directly access the bistability with spontaneous vibrations regime with thermal fluctuations. In some embodiments, a new class of nanomechanical devices, nanovibrators, may be constructed by using an unexpected effect of thermally activated vibration of bistable oligomeric machines. FIG. 10 is a diagrammatic representation of this principle wherein (1000) depicts an energic profile of a bistable system which vibrates between a bent (1001) and stretched (1002) state. Elements (1003), (1004), (1005), (1006), (1007), (1008) and (1009) of FIG. 10 depict a stretched conformation, a fixed edge, a rigid element, a bending or hinge region, a rigid element, an applied force, and vibratory action respectively. A preferred nanomechanical embodiment may be an oligo-NIPMA-30 or oligo-NIPAm-20 compositions consisting of two persistent Kuhn segments of about 1 nanometer in length joint by a bending or hinge location. The dynamics of oligomeric machines subject to the action of pulling forces were studied by computer simulation methods. GROMACS molecular dynamics package were used to perform atomistic simulations of oligomeric machines in water above a critical temperature. OPLS-AA force field in combination with TIP3P explicit water model are used to describe inter- and intra-molecular interactions. The dynamics of oligomeric machines are characterized by the time dependence of the edge-to-edge distances in the chain. Thermally induced spontaneous vibrations of the oligomeric machines are established by fine-tuning control of the pulling force near a threshold value. FIG. 11 illustrates an exemplary embodiment and shows the time dependence of the edge-to-edge distances in oligo-NIPMAm-30 oligomer in a vibration regime near the critical pulling force Fc=400 pN. In the vicinity of a threshold value of pulling force for exemplary embodiments oligo-NIPMAm-30 and NIPAm-20, the oligomers alternately visit both the open and closed states. The vibration between these states occurs for rather small deviations of the pulling force, up to 20 pN, from 400 pN for oligo-NIPMAm-30 and from 120 pN for NIPAm-20 oligomer. FIG. 12 demonstrates for these exemplary embodiments that for larger deviations such as when the bistable potential is highly asymmetric, the oligomeric machines are stuck in one of the two states and no vibration is produced. FIG. 12 depicts statistics of visits to bent and stretched states normalized on the maximum value for an exemplary oligo-NIPMAm-20 embodiment near (1200) and far from (1201) a critical pulling force respectively. Curves (1202), (1203), (1204), (1205), (1206), and (1207) correspond to forces of 280 pN, 300 pN, 320 pN, 230 pN. 250 pN, and 280 pN respectively. In some exemplary embodiments, non-covalent interactions may be used to modulate this bistable vibratory behavior. FIG. 13 illustrates an exemplary embodiment, where hydrogen bonding along the chain of oligo-NIPMAm-30 and between the oligo-NIPMAm-30 and surrounding water modulates the vibration. Surprisingly in these exemplary embodiments, no correlations between the number of hydrogen bonds surrounding the edge parts of NIPMAm-30 chain and the vibration is observed. FIG. 13 depicts an exemplary embodiment for NIPMAm-30 oligomer and shows time dependence of number of hydrogen bonds surrounding a hinge location in the top curves (1300 and 1302) and edge-to-edge distance of the chain in the bottom curve (1301 and 1303) for pulling forces of Fc=400 pN in the left panel (1300 and 1301) and F=500 pN in the right panel (1302 and 1303). Such embodiments show that the hydrogen bonds surrounding a hinge location of a NIPMAm-30 oligomer play a dominate role in the mechanic-like vibration of the oligomeric machine. In this embodiment, an oligomeric machine alternately visits two states with the time interval of about 5 nanoseconds in average, which corresponds to jumping over an activation barrier of about 10 kBT and the vibrations are modulated by commutations of about 1 hydrogen bond in the hinge location area. Thermally induced spontaneous vibrations reveal an important feature of some embodiments of molecular and/or oligomeric machines. The mechanic-like movement of such embodiments is well-distinguished from thermal fluctuations, but at the same time, the machine action may be activated even by low-potential thermal energy.

Additional Embodiments of Oligomeric Machines for Energy Harvesting

In some embodiments, an oligomeric machine comprises a first oligomeric module having a first end and a second end, and a second oligomeric module having a first end and a second end; wherein the first end of the first oligomeric module is joined to the first end of the second oligomeric module; and wherein the oligomeric machine exhibits dynamical bistability, spontaneous vibrations and/or stochastic resonance in a solution at a temperature when the temperature is in a critical temperature range and the oligomeric machine does not exhibit stochastic resonance in the solution when the temperature is not in the critical temperature range; and wherein the oligomeric machine exhibits dynamical bistability, spontaneous vibrations, and/or stochastic resonance in a solution under a force load applied to the oligomeric machine when the force load is in a critical force range while the temperature is not in a critical temperature range, and the oligomeric machine does not exhibit dynamical bistability, spontaneous vibrations, and stochastic resonance in the solution when both the force load and the temperature are not in the critical ranges.

Dynamical bistability, spontaneous vibrations and/or stochastic resonance are characterized by an oligomeric machine repeatedly fluctuating spontaneously or regularly between a first conformation and a second conformation. A conformation of an oligomeric machine may be characterized by the relative orientation and displacement of the respective second ends of the first and second oligomeric modules. If a bistable system is perturbed by random impacts, and if these perturbations are sufficiently strong relatively to the bistability barrier, the system will jump between two energy minima performing spontaneous vibrations. Stochastic resonance is the regularization of spontaneous vibrations by a weak oscillating force applied to the bistable system. That is, by apply a weak oscillating force to a system in a spontaneous vibrations regime, random jumps between two states characteristic of spontaneous vibrations may be transformed into more regular jumps characteristic of stochastic resonance.

Oligomeric modules are oligomers comprising a few and/or many repeated monomeric residues. Oligomers may comprise one or many types of monomeric residues. For instance, oligomers may comprise one, two, three, or more types of monomeric residues. The types of monomers may not be particularly limited so long as the oligomeric machines exhibit spontaneous vibrations and stochastic resonance in solution in a critical temperature or/and under a critical force load applied to the oligomeric machine. For instance, monomeric residues may comprise optionally substituted acrylamide residues, optionally substituted (meth) acrylamide residues, optionally substituted (meth)acrylic acid residues, optionally substituted aziridine residues, optionally substituted epoxy residues, alkoxy substituted ethane residues, or combinations thereof. In general, the term "substituted" refers to the replacement of hydrogen radicals in a given structure with the radical of a specified substituent such as a $C_1$-$C_8$ alkyl group. In preferred embodiments, monomeric residues are chosen from N-ethylacrylamide residues, 2-(isopropylcarbamoyl)acrylic acid residues, 1-(aziridin-1-yl)-2-methylpropan-1-one residues, methoxyethene residues, and 2-methyloxirane residues, and combinations thereof.

Oligomers may be synthesized by a variety of methods. The synthesis of oligomers is not particularly limited and some exemplary techniques include iterated synthesis, step growth syntheses, polymerization reactions, living polymerizations, living radical polymerizations, atom transfer radical polymerization, anionic polymerizations, cationic polymerizations, reversible addition fragmentation chain transfer polymerizations, ring open polymerization, metathesis reactions, and/or solid supported synthesis. Oligomers may be synthesized in a single reaction or multiple reactions. Purification techniques may be used to fractionate and/or separate oligomers by, for example, molecular weight, functionality, tacticity, stereochemistry, and/or regiochemistry. Oligomers may contain more than one monomer type and may have various architectures such as block-co-oligomers, branched oligomers, random-co-oligomers, and/or gradient oligomers. Oligomers may be coupled together through a variety of means such as for instance click chemistry, azo-alkyne chemistry, thiol-ene chemistry, epoxy chemistry, Diels-Alder reactions, chain-end substitutions, and/or may be synthesized together in a single and/or multiple reaction steps. Oligomers may be telechelic. The tacticity may be controlled through various means such as, for example, though catalyst selection, solvent selection, reaction temperature, ligand selection, and/or polymerization reaction selection. The molecular weight of oligomers may be controlled by controlling reaction temperature, monomer concentration, initiator concentration, inhibitor concentration, reaction duration, post synthetic separation, and/or reactions may be quenched.

Oligomers and/or oligomeric machines may be coupled to surfaces and/or solid supports through a variety of means such as for instance click chemistry, azo-alkyne chemistry, thiol-ene chemistry, epoxy chemistry, Diels-Alder reactions, silane chemistry, and/or may be synthesized on a surface and/or solid supports in a single and/or multiple reaction steps. An oligomeric machine may be immobilized on a suitable organic or metal surface by fixing one end of the oligomeric machine on the surface and leaving the other end to move under compression or pulling forces. An oligomeric machine may have a charge such as a net positive or net negative charge associated with one end, and the second end of the oligomeric machine may be immobilized on a suitable surface such as, for example, an organic or metal surface. An electric field may be applied to the oligomeric machine so as to apply a force load to the oligomeric machine. The electric field may be constant with time or may change with time. The electric field may be periodic having a magnitude and a frequency. The electric filed may be oriented along a long axis of the oligomeric machine. In some embodiments, a net negative charge may be associated to one end of an oligomeric machine using one or more carboxylic acid groups. In some embodiments, a net positive charge may be associated to one end of an oligomeric machine using amine groups. In some embodiments, an oligomeric machine may be immobilized on a surface using, for example, thiol groups, silane groups, or nitrene chemistry. In some embodiments, an oligomeric machine may be synthesized from an initiator group attached to a surface.

Some exemplary embodiments include oligomers comprising N-isopropylacrylamide (NIPAm) and/or N-isopropylmethacrylamide (NIPMAm), Some exemplary embodiments include block-co-oligomers of N-isopropylacrylamide and/or N-isopropylmethacrylamide. Some exemplary embodiments include block-co-oligomers of N-isopropylacrylamide and/or N-isopropylmethacrylamide with one or more isotactic, atactic, and/or syndiotactic blocks. Some oligomers comprise at least 10, at least 15, at least 20, at least 25, and/or at least 30 monomeric units. In some embodiments, the first and second oligomeric modules each comprise from 10 to 30 repeat units. Some oligomers have a persistence length of at least 0.5 nm, at least 1 nm, and/or at least 2 nm. Some oligomers may be at least 0.5 nm, at least 1 nm, at least 2 nm, at least 5 nm, and/or at least 10 nm long. In some embodiments, the first and second oligomeric modules each have a persistence length from 0.5 nm to 20 nm. In some embodiments, the first end of the first oligomeric module is joined to the first end of the second oligomeric module through a linker unit having a persistence length that is less than the persistence length of both the first and second oligomeric modules.

Some oligomers may possess a lower critical solution temperature (LCST). Some oligomers may possess an upper critical solution temperature (UCST). Bulk poly(N-isopropylacrylamide) (PNIPAm) exhibits a LCST. The LCST of an oligomer may be different than the LCST of a longer polymer made from the same monomeric units. The LCST of an oligomer may be changed by changing the composition of the oligomer. The LCST of an oligomer may be changed by tuning the ratio of comonomers in an oligomer. Some oligomers may be polydisperse. Some oligomers may be monodisperse. Some oligomers may not possess any significant polydispersity. Some exemplary embodiments may comprise oligomeric fragments of PNIPAm of 20-30 units and PNIPMAm (poly-N-isopropylmethacrylamide) of the same length. Some embodiments comprise block-co-oligomer compositions with a central PNIPAm fragment of 5-15 units and two terminal PNMIPAm fragment of 5-20 units. Such exemplary embodiments may be configured to exhibit two clearly discernible conformational states, one of which corresponds to an unfolded, stretched form of oligomeric fragment, while the other has a folded, bent form. Transitions between these conformational states in these exemplary embodiments implement mechanic-like nanoscale motions of the fragment parts.

Oligomeric modules may be joined together. Oligomeric modules may be joined together during the synthesis of the oligomeric modules. Oligomeric modules may be joined together in a subsequent reaction. Oligomeric modules may be joined together at a bending and/or hinge region. The bending and/or hinge region may be inherent to the oligomeric structure. The bending and/or hinge region may comprise an additional molecular and/or oligomeric structure. The bending and/or hinge region may comprise a residue product from a linking reaction such as, for example, a click reaction, chain-end modification reaction, a thiol-ene reaction, an azo-alkyne reaction, a Diels-Alder reaction, an epoxy reaction, a esterification reaction, and/or a cycloaddition reaction. A bending and/or hinge region may be flexible. A bending and/or hinge region may comprise, for example, acrylamide residues, methacrylamide residues, ether linkages, ethylene oxide units, peptides, and/or peptoids. In some embodiments, an oligomeric machine comprises at least one bending or hinge location at a position of co-joinder between the first oligomeric module and the second oligomeric module, the bending or hinge location permitting relative flexure between the first oligomeric module and the second oligomeric module.

Oligomeric machines may be configured to exhibit stochastic resonance and/or spontaneous vibrations in solution when the solution is in a critical temperature range and the oligomeric machine does not exhibit stochastic resonance and/or spontaneous vibrations in solution when the solution is not in the critical temperature range. Oligomeric machines may comprise oligomeric modules selected and joined so as to exhibit stochastic resonance in solution when the solution is in a critical temperature range and the oligomeric machine does not exhibit stochastic resonance in solution when the solution is not in the critical temperature. Oligomeric machines may comprise oligomeric modules selected and joined so as to exhibit stochastic resonance and/or spontaneous vibrations in solution when the solution is in a critical temperature range and the oligomeric machine does not exhibit stochastic resonance and/or spontaneous vibrations in solution when the solution is not in the critical temperature.

Oligomeric machines may be configured to exhibit stochastic resonance and/or spontaneous vibrations in solution under a force load applied to the oligomeric machine when the force load is in the critical force range, and the oligomeric machine does not exhibit stochastic resonance and/or spontaneous vibrations in solution when the force load in not in the critical force range. Oligomeric machines may comprise oligomeric modules selected and joined so as to exhibit stochastic resonance and/or spontaneous vibrations in solution under a force load applied to the oligomeric machine when the force load is in the critical force range, and the oligomeric machine does not exhibit stochastic resonance and/or spontaneous vibrations in solution when the solution is force load in not in the critical force range.

A critical temperature is a temperature about which an oligomeric machine displays stochastic resonance and/or spontaneous vibrations, and a critical temperature range is a range of temperatures including the critical temperature wherein the oligomeric machine displays stochastic resonance and/or spontaneous vibrations. A critical temperature range may be within a temperature range given by 250 K to 400 K, 275 K to 375 K, and/or 300 K to 350 K. A critical temperature range may be within a temperature range given by −25° C. to 100° C., 0° C. to 100° C., and/or 25° C. to 100° C. A critical temperature range may be within a temperature range given by 25° C. to 45° C. A critical temperature range may be increased or decreased by changing the composition of the solution. For example, a critical temperature range may be increased or decrease by changing the ionic strength, pH, and/or weight percent of solvents and/or co-solvents in the solution.

A critical force load is a force load about which an oligomeric machine displays stochastic resonance and/or spontaneous vibrations, and a critical force range is a range of force loads including the critical force load wherein the oligomeric machine displays stochastic resonance and/or spontaneous vibrations. A critical force range may be within a force range given by 25 pN (pico-Newton) to 200 pN, 100 pN to 350 pN, and/or 300 pN to 450 pN. A critical force range may be within a force range given by 370 pN to 400 pN. A critical force range may be increased or decreased by changing the composition of the solution. For example, a critical force range may be increased or decrease by changing the ionic strength, pH, and/or weight percent of solvents and/or co-solvents in the solution.

A solution may be an aqueous solution. Aqueous solutions may comprise one or more salts such as, for example, halide salts such as sodium chloride or phosphate salts such as sodium phosphate. Aqueous solutions may comprise one or more buffers such as, for example, phosphate buffered saline, tris buffer, acetate buffer, HEPES buffer, Good's buffers. An aqueous solution may be a body fluid. An aqueous solution may be a body fluid derived from a subject such as a human subject. An aqueous solution may be a blood sample. An aqueous solution may be a saliva sample.

Oligomeric machines capable of exhibiting conformation bistability may comprise electric generating elements and may be configured to actuate an electric generating element. An electric generating element may be, for example, a piezoelectric element, a nanoparticle, a nanolayer, and/or a nanotube. An oligomeric machine may be configured such that as the oligomeric machine transitions from a first conformation to a second conformation, the oligomeric machine applies a stress to the electric generating element such as, for example, a piezoelectric element. The stress may include a compressive force, a tensile force, or a shear force. An oligomeric machine may be configured to apply a stress to an electric generating element in various ways. An oligomeric machine may be configured such that as the oligomeric machine transitions from a first conformation to a second conformation it applies a compressive stress to a piezoelectric element thus generating a voltage. An electric generating element may be attached covalently or noncovalently to an oligomeric machine. An electric generating element may be attached covalently or noncovalently to an oligomeric machine at a bending and/or hinge location. An electric generating element may be attached covalently or noncovalently to an oligomeric machine at a bending and/or hinge location such that as an oligomeric machine transitions from an open conformation to a closed or folded conformation, the oligomeric machine applies a stress to the electric generating element.

Oligomeric machines capable of exhibiting conformation bistability may comprise photo-absorbing elements and may be configured to change conformation upon absorption of light energy. Photo-absorbing elements may comprise, for example, one or more dye molecules, a conjugated molecule, an aromatic molecule, a semiconducting oligomer and/or polymer, a quantum dot, a nanoparticle, a stilbene moiety, an azobenzene moiety, and/or a bond configured for cis-trans isomerization. Oligomeric machines capable of exhibiting conformation bistability may comprise photo-absorbing elements at one or more bending and/or hinge regions. Oligomeric machines capable of exhibiting conformation bistability may comprise a bond configured for cis-trans isomerization at one or more bending and/or hinge regions such that upon absorption of light, the bond configured for cis-trans isomerization isomerizes thus inducing a conformational change of the oligomeric machine. A bond configured for cis-trans isomerization bond may be incorporated into an oligomeric machine, for example, by a polymerization reaction off of a bifunctional initiator comprising a bond configured for cis-trans isomerization.

Figure 14A:
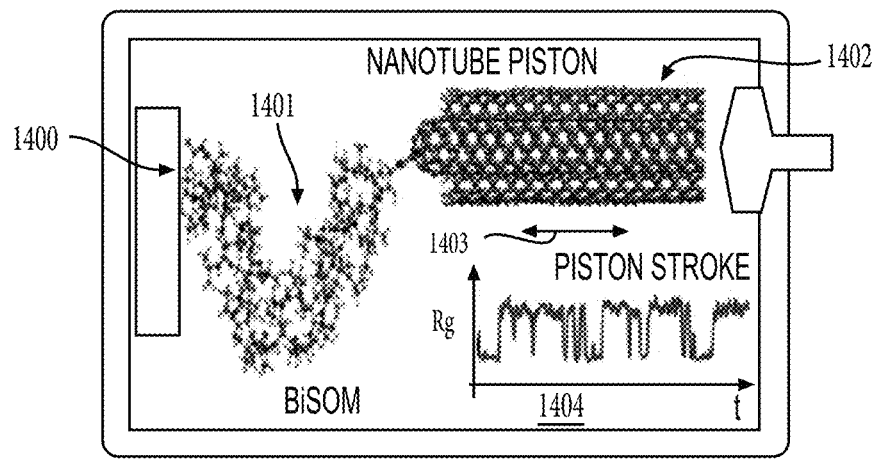
FIG. 14A depicts an exemplary nanomachine embodiment that acts like a piston type engine comprising a bistable oligomeric machine connected to two nanotubes, one of which is reversibly moved inside the other.

An oligomeric machine may comprise a piston type element. A piston type element may be a rigid molecular structure such as a nanotube and/or a molecular structure possessing a persistence length greater that 10 nm. An oligomeric machine may be attached to a surface on one end and a rigid molecular structure on a second end. An oligomeric machine may be configured such that a change in conformation results in a mechanical actuation of a rigid molecular structure. An oligomeric machine may be attached to a surface using, for example, thiol chemistry, silane chemistry, and/or nitrene chemistry. An oligomeric machine may be synthesized on a solid support. An oligomeric machine may be attached to a rigid molecular structure using, for example, thiol chemistry, click chemistry, and/or nitrene chemistry. An oligomeric machine may be synthesized on a rigid molecular structure. An oligomeric machine may be synthesized on and/or attached to a solid support and may comprise an end functionalization configured to bind a rigid molecular structure. A rigid molecular structure may be configured to bind with and/or react with an end functionalized oligomeric machine. In some embodiments, oligomeric compositions of a few nanometers in size, which possess the property of conformational bistability, may be used as power units in an oligomeric machine. A nanomechanical device of the piston engine type with a bistable oligomeric composition that acts as a power unit is depicted in FIG. 14A wherein (1400) depicts an exemplary attaching point to a surface, (1401) depicts an exemplary oligomeric machine component, (1402) depicts an exemplary piston type element, (1403) depicts an exemplary actuation cycle, and (1404) depicts an exemplary radius of gyration vs time. Such an embodiment may comprise a complex composition constructed from three constructive elements. Two elements may be two nanotubes coaxially inserted one into the other like a piston in a cylinder. The inner nanotube is movable and acts as a piston, while the outer nanotube is stationary and acts as a cylinder. The third functional element of the nanomechanical device may comprise a bistable oligomer, one end of which is fixed, while the other end is connected to the inner nanotube of the piston-nanotube structure.

Figure 14B:
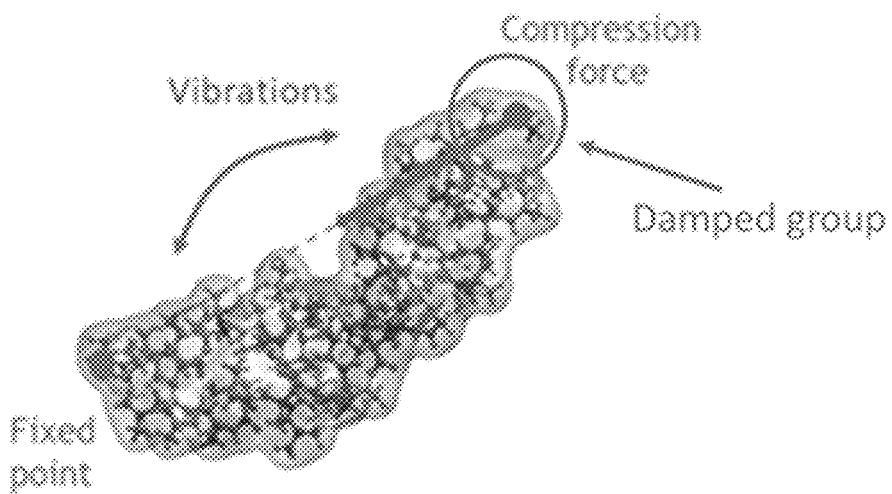
FIG. 14B depicts an exemplary system comprising oligo-PNIPMAm-30 having one end fixed and one end damped.
Figure 14C:
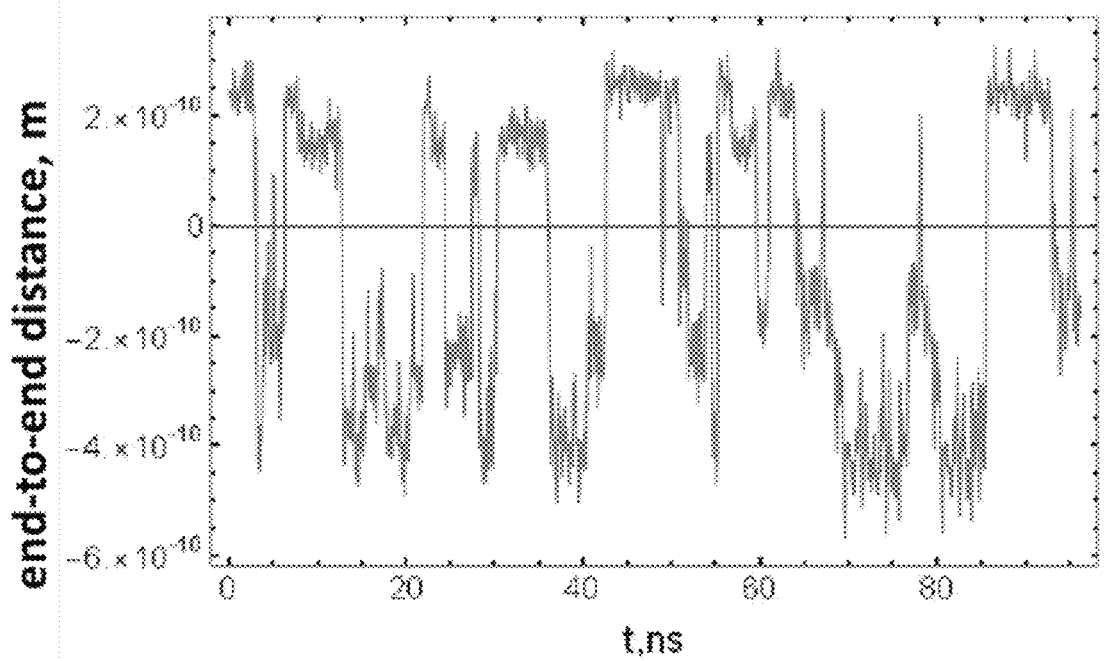
FIG. 14C depicts spontaneous vibrations of an exemplary system comprising oligo-PNIPMAm-30.
Figure 14D:
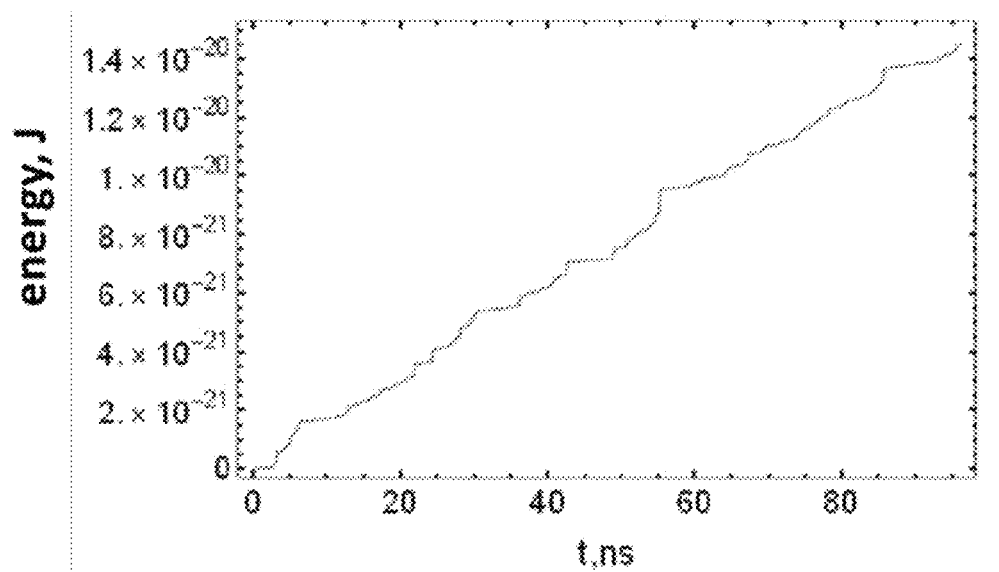
FIG. 14D depicts energy extracted from an exemplary system comprising oligo-PNIPMAm-30 by a damping group.
Figure 14E:
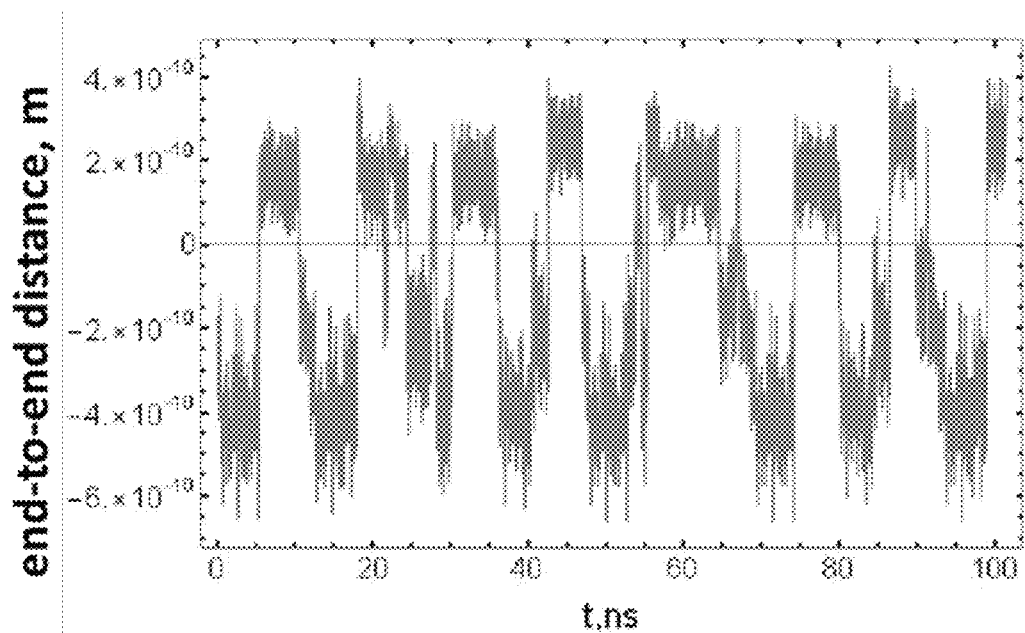
FIG. 14E depicts stochastic resonance of an exemplary system comprising oligo-PNIPMAm-30 in an external harmonic field V=0.2 V/nm, frequency=100 MHz.
Figure 14F:
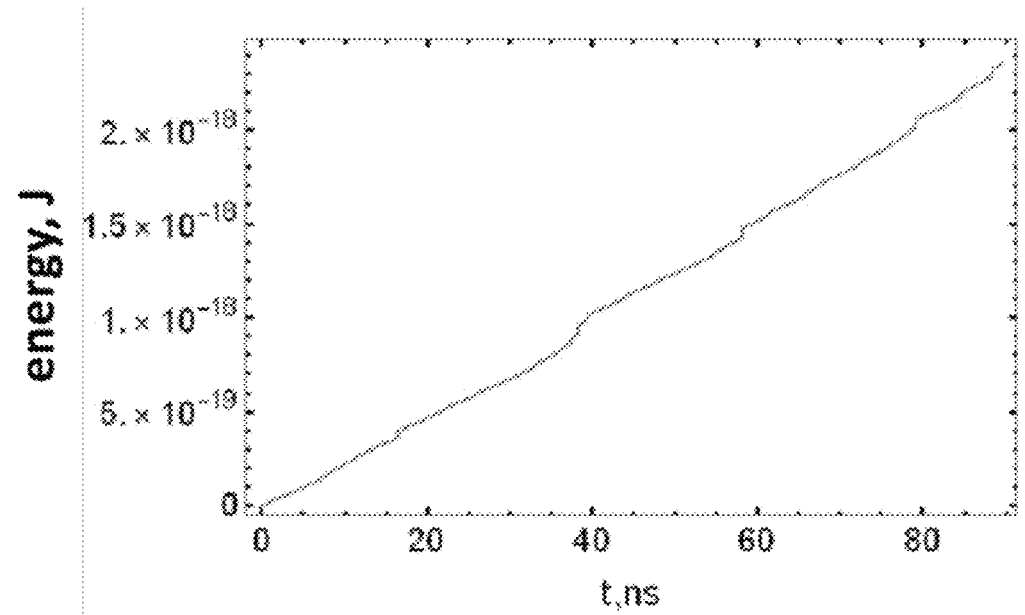
FIG. 14F depicts energy extracted from an exemplary system comprising oligo-PNIPMAm-30 by a damping group.
Figure 14G:
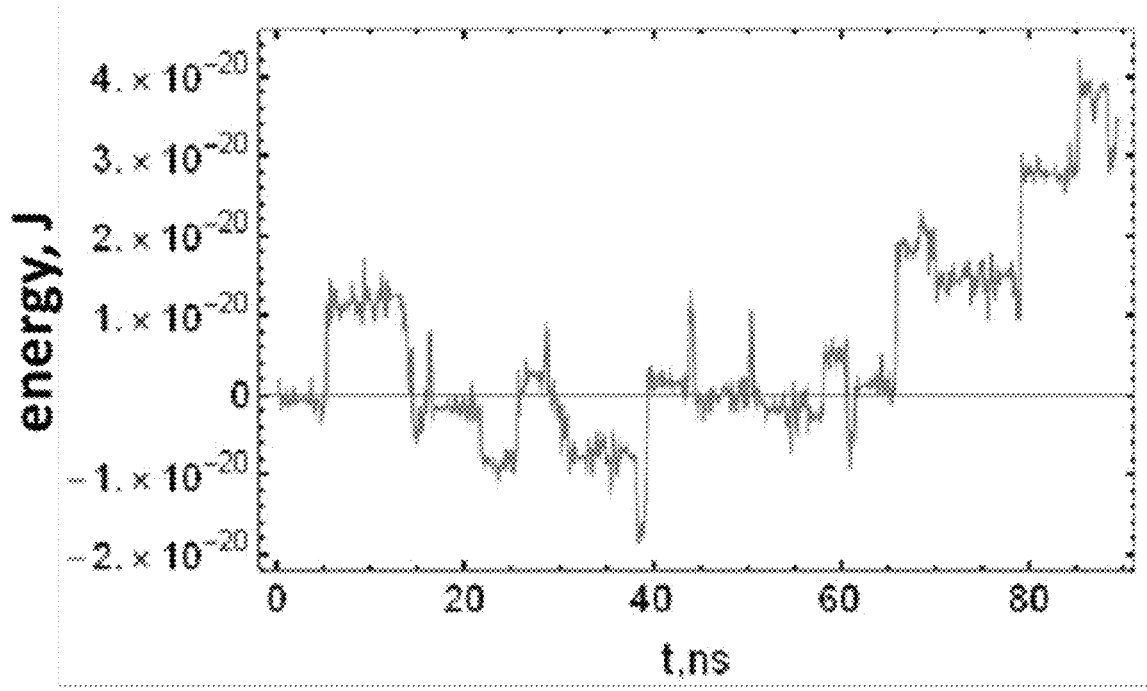
FIG. 14G depicts energy pumped into an exemplary system comprising oligo-PNIPMAm-30 by an external harmonic field.

An oligomeric machine may have one end fixed and one end damped. A damping group is a group which damps the motion of an oligomeric machine. A damping group may or may not be a piston type element. FIG. 14B depicts an exemplary embodiment comprising an oligo-PNIPMAm-30 oligomeric machine having one end fixed and one end damped with a damping group. The damping coefficient for atoms of a damped group is 10 psec-1. The damping coefficient for all other atoms is 0.5 psec-1. A compressive force for the spontaneous vibration regime is 393 pN. FIG. 14C depicts spontaneous vibrations of an exemplary system comprising oligo-PNIPMAm-30. FIG. 14D depicts energy extracted from an exemplary system comprising oligo-PNIPMAm-30 by a damping group. FIG. 14E depicts stochastic resonance of an exemplary system comprising oligo-PNIPMAm-30 in an external harmonic field V=0.2 V/nm, frequency=100 MHz. FIG. 14F depicts energy extracted from an exemplary system comprising oligo-PNIPMAm-30 by a damping group. FIG. 14G depicts energy pumped into an exemplary system comprising oligo-PNIPMAm-30 by an external harmonic field.

Figure 15:
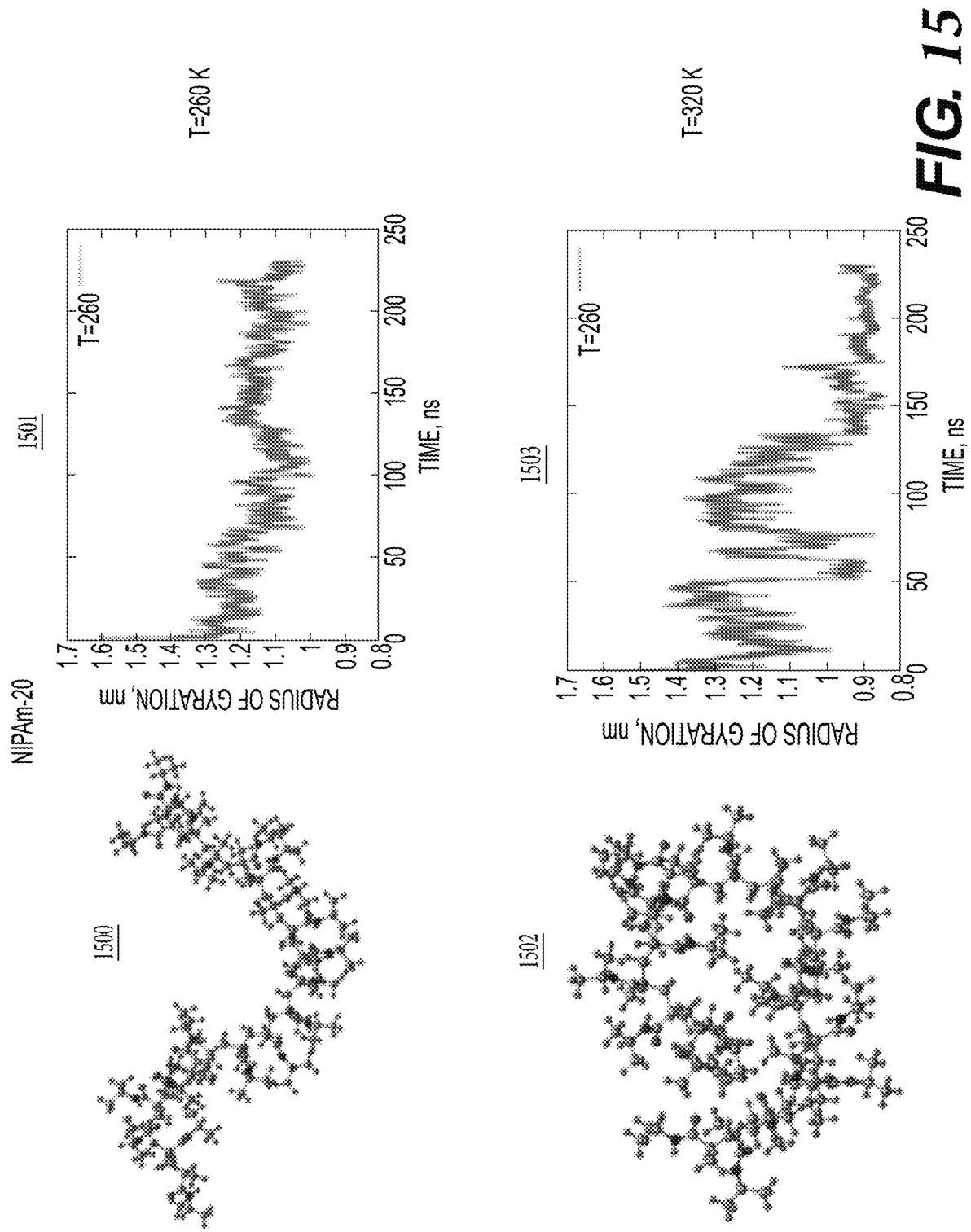
FIG. 15 depicts unfolded (2000) and folded (2002) shapes of an exemplary NIPAm-20i embodiment.

Non-Limiting Exemplary Embodiments of Oligomeric Machines and Applications Thereof In some embodiments, PNIPAm oligomers, being of a length about two joint Kuhn segments, may undergo a reversible conformational change when the solute's temperature passes over a LCST, thus reproducibly changing mutual orientation of the Kuhn segments. This may be demonstrated using a series of computational experiments. Full atomic GROMACS molecular dynamics package were used to perform atomistic simulations of a NIPAm-oligomer in water solution at temperatures below and above LCST. OPLS-AA force field in combination with TIP3P explicit water model are used to describe inter- and intra-molecular interactions. The conformation of the chain is characterized by its radius of gyration and/or the distance between the chain ends. In an exemplary embodiment, an oligomer may comprise 20 NIPAm monomeric units connected isotactically (named oligo-NIPAm-20). FIG. 15 depicts an exemplary embodiment of oligo-NIPAm-20i wherein the chain is unfolded at the temperature of 280K with an average gyration radius of 1.20 nm (1500 and 1501), and it folds at the temperature of 320K to a state with an average gyration radius of 0.90 nm (1502 and 1503).

For some embodiments, 25-30 monomeric units connected syndiotactically is optimal, and it seemingly corresponds to approximately two persistent Kuhn segments. For instance, an oligomer consisting of 15 NIPAm monomers connected syndiotactically (named oligo-NIPAm-15s) does not show conformational bistability in response to temperature change, having gyration radius of 0.97 nm at 280K and 0.98 nm at 320K.

Figure 16:
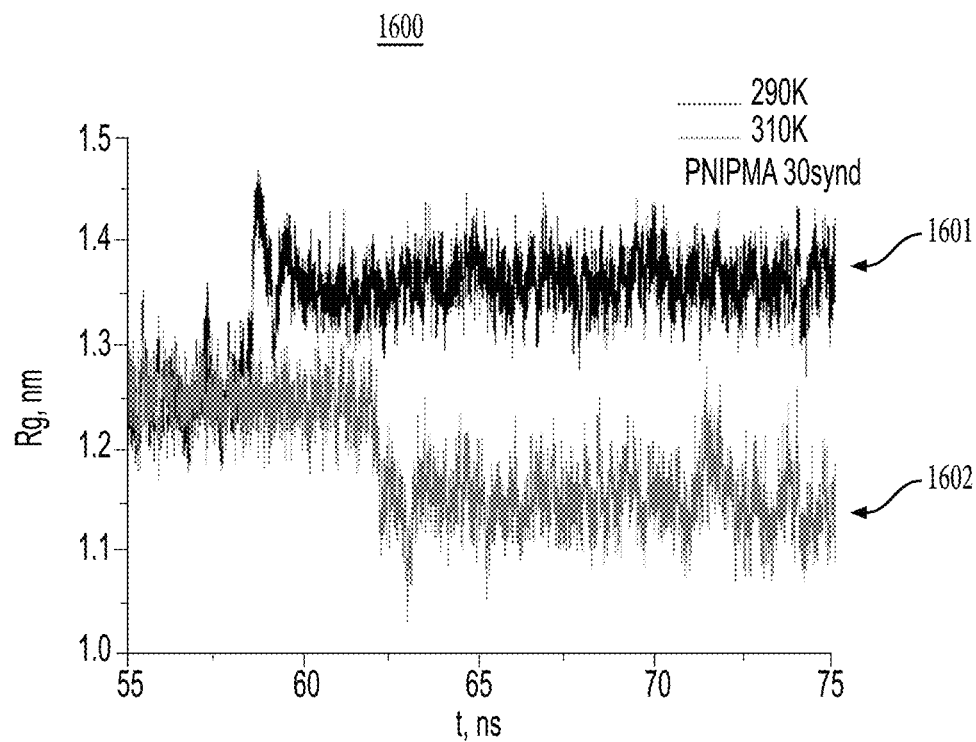
FIG. 16 depicts the radius of gyration vs simulation time for an exemplary NIPMAm-30s embodiment.
Figure 17:
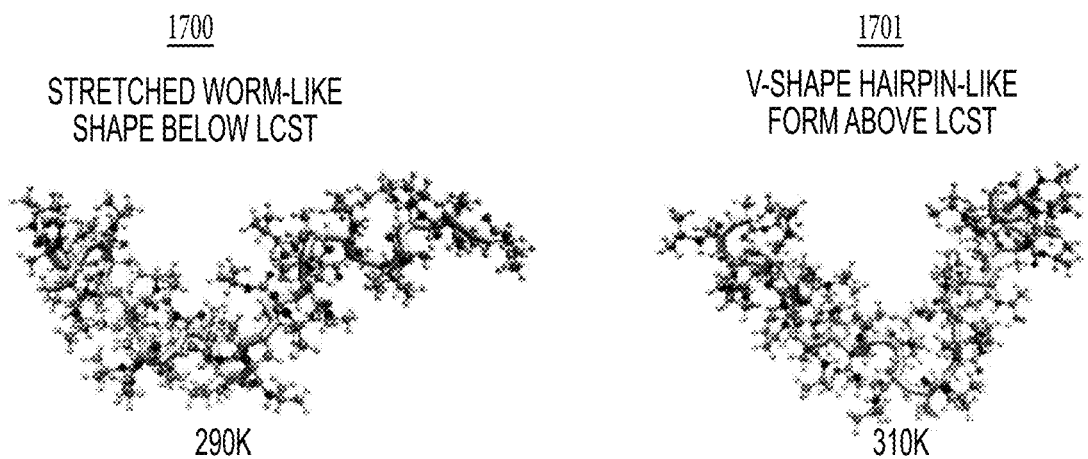
FIG. 17 depicts unfolded (2200) and folded (2201) shapes of an exemplary NIPMAm-30s embodiment.

Poly-(N-isopropyl)-methacrylamide (PNIPMAm) is also a thermosensitive polymer that has an LCST at approximately 315K (42° C./108° F.). In some embodiments PNIPMAm oligomers, being of a length about two joint persistent Kuhn segments, may be configured to undergo a conformational change from unfolded to folded states when a solute's temperature passes over the transition point. GROMACS molecular dynamics package was used to perform full atomistic simulations of single PNIPMAm oligomers in water at temperatures below and above LCST. OPLS-AA force field in combination with TIP3P explicit water model is used to describe inter- and intra-molecular interactions. The critical temperature for some oligomers is lower than the LCST for bulk polymers. In some embodiments, it is expected to be between 305K and 310K. FIG. 16 and FIG. 17 depicts an exemplary oligomer embodiment comprising 30 NIPMAm monomers connected syndiotactically (named oligo-NIPMAm-30s) and demonstrates an unfolded chain at the temperature of 290K with an average gyration radius of 1.35 nm (1601), and it folds at the temperature of 310K with an average gyration radius of 1.15 nm (1602). FIG. 17 depicts an exemplary oligomer's conformational change from worm-like unfolded shape (1700) to V-shaped hairpin-like folded structure (1700).

Figure 18:
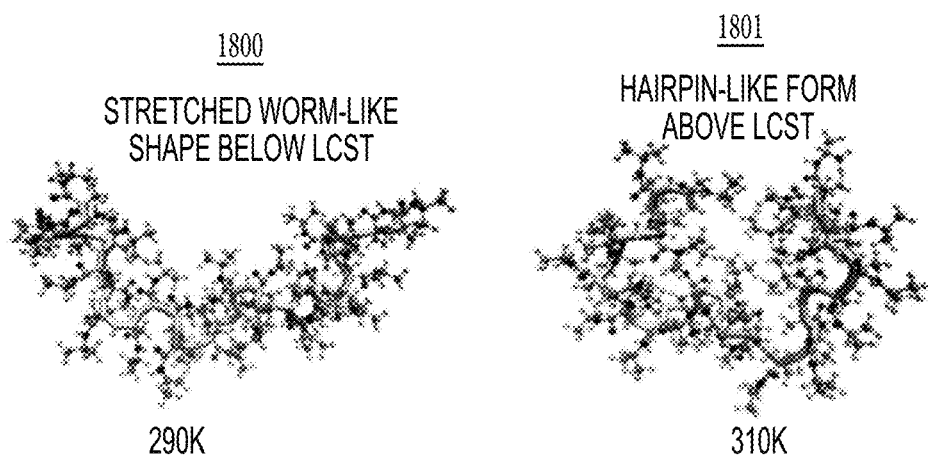
FIG. 18 depicts unfolded (2300) and folded (2301) shapes of an exemplary NIPMAm-30i embodiment.
Figure 19:
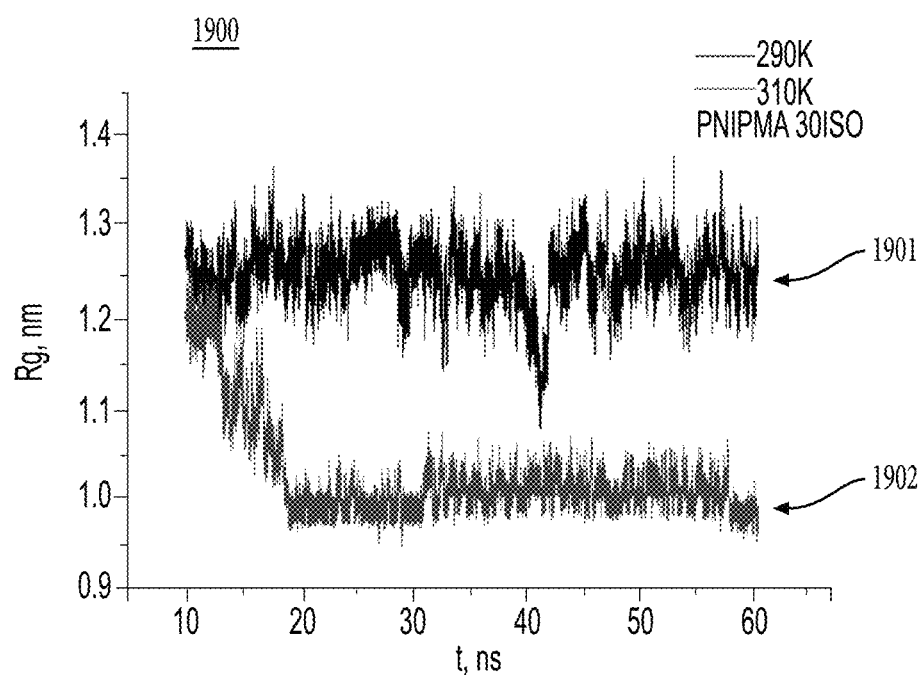
FIG. 19 depicts radius of gyration vs simulation time for an exemplary NIPMAm 30i embodiment.

In an exemplary embodiment, FIG. 18 depicts an oligomer comprising 30 NIPMAm monomers connected isotactically (named oligo-NIPMAm-30i). In this embodiment, FIG. 19 shows that the chain is unfolded at the temperature of 290K with an average gyration radius of 1.37 nm (1901), and it folds at the temperature of 310K with an average gyration radius of 1 nm (1902). In this embodiment, the oligomer chain's conformation changes from stretched worm-like shape (1800) to folded hairpin-like shape (1801).

Figure 20:
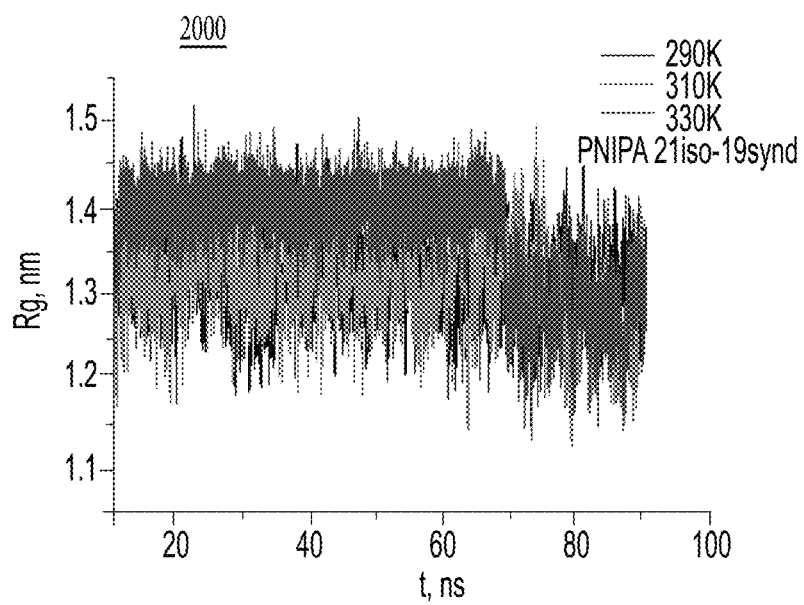
FIG. 20 depicts radius of gyration vs simulation time for an exemplary NIPAm-21i-19s di-block embodiment.

It may be demonstrated that some oligomeric structures do not demonstrate conformational bistability. For example, an oligomer consisting of a block of 21 NIPAm monomers connected isotactically, and a block of 19 NIPAm monomers connected syndiotactically (named oligo-NIPAm-21i-19s) does not demonstrate thermosensitive folding as shown in FIG. 20. In simulations performed on NIPMAm's oligomers consisting of 20 monomers connected atactically (named oligo-NIPMAm-20a) and syndiotactically (named oligo-NIPMAm-20s). Both oligomers do not show conformational bistability. At temperatures below and above LCST, they have average radii of gyration of 1 nm for oligo-NIPMAm-20a and 0.8 nm for oligo-NIPMAm-20s. An oligomer consisting of 30 NIPMAm monomers connected atactically named oligo-NIPMAm-30a, takes a stretched unfolded shape at the temperature of 290K with an average gyration radius of 1.57 nm, while at the temperature of 310K it has slightly more compact worm-like shape with an average gyration radius of 1.35 nm. Simulations were also performed on NIPMAm's oligomers consisting of 20 monomers connected atactically, named oligo-NIPMAm-20a, and syndiotactically, named oligo-NIPMAm-20s. Both oligomers do not show conformational bistability and at temperatures below and above the LCST, they have average radii of gyration of 1 nm for oligo-NIPMAm-20a and 0.8 nm for oligo-NIPMAm-20s.

Figure 21:
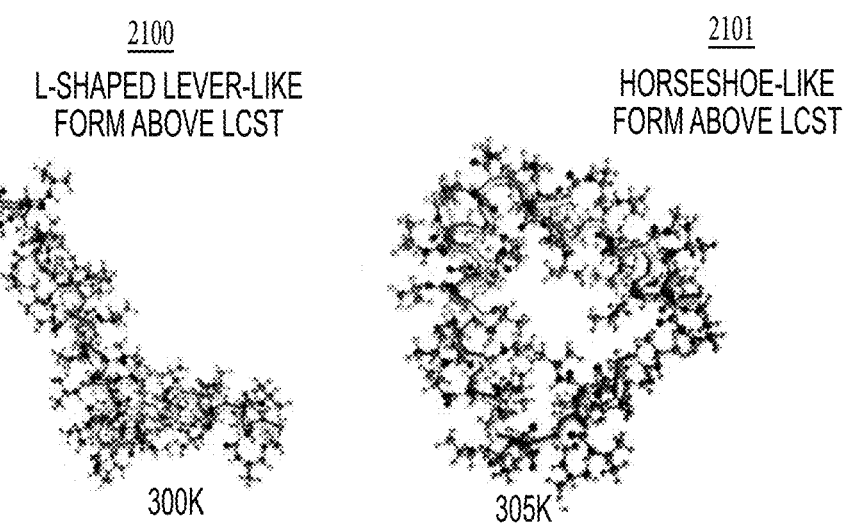
FIG. 21 depicts unfolded (2600) and folded (2601) shapes of an exemplary NIPAm-21i-19a di-block embodiment.
Figure 22:
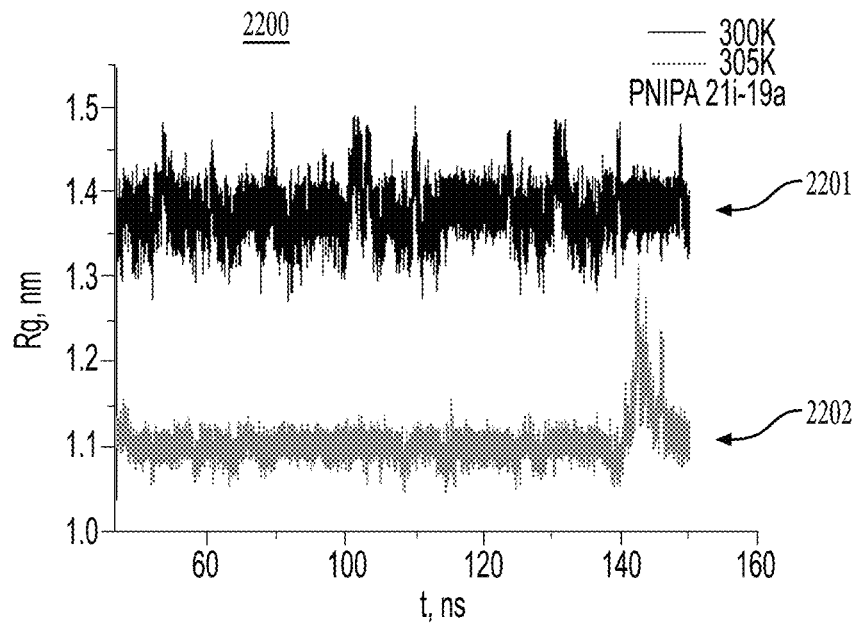
FIG. 22 depicts radius of gyration vs simulation time for and exemplary 21i-19a NIPAm di-block embodiment.

In some exemplary embodiments illustrated in FIG. 21, an oligomer may comprise two joined persistent blocks differing in tacticity and comprising a block of 21 NIPAm monomers connected isotactically and a block of 19 NIPAm monomers connected atactically (herein named oligo-NIPAm-21i-19a). This structure exhibits conformational bistability in response to temperature change wherein below a LCST it adopts an unfolded extended shape with an average radius of gyration of 1.37 nm (2100), and above LCST, the oligomer folds in to a horseshoe-like shape with an average radius of gyration of 1.1 nm (2101). FIG. 22 further illustrates this exemplary embodiment wherein small fluctuations in the radius of gyration relative to its variation in the folded (2202) and unfolded (2201) states show that these states are well defined.

Figure 23:
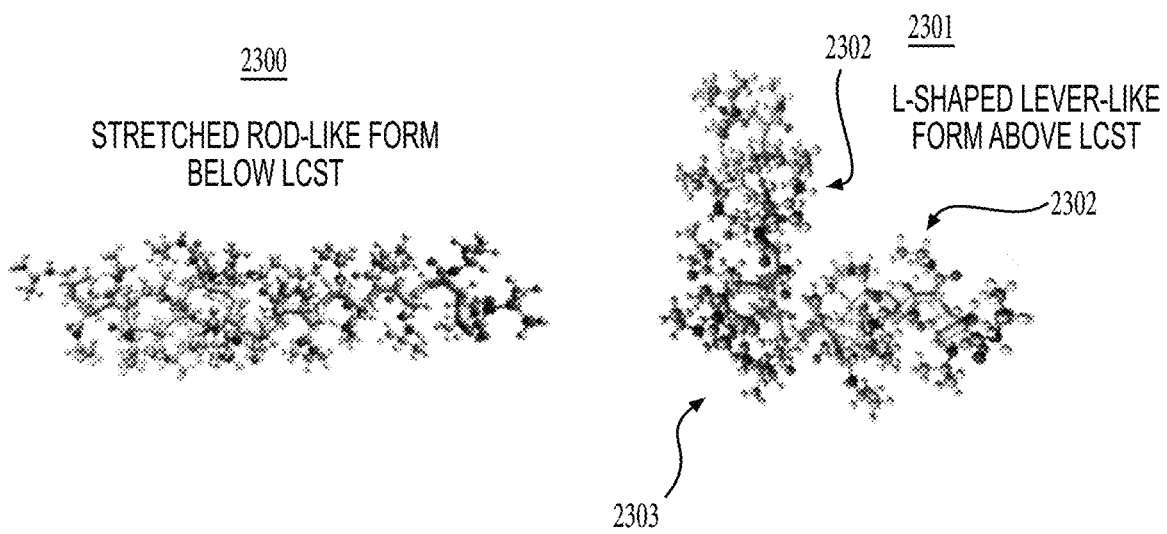
FIG. 23 depicts unfolded (2800) and folded (2801) shapes of an exemplary NIPAm-12i-4s-12i tri-block embodiment.

In another exemplary embodiment, an oligomeric machine component comprising two stiff fragments of about 10 isotactic NIPAm units joined by a bending or hinge location of syndiotactic NIPAm is demonstrated. In a preferred three-block oligomeric machine comprising two edge blocks, each of 12 NIPAm monomers connected isotactically, which are joined by the bending location composed of 4 NIPAm monomers connected syndiotactically. This composition is denoted oligo-NIPAm-12i-4s-12i. Below the LCST, the oligo-NIPAm-12i-4s-12i composition exists predominately in a stretched rod-like structure with an average gyration radius of 1.3 nm. Above the LCST, this three-block oligomeric machine folds into an L-shaped lever-like form with an average radius of gyration of 1.05 nm. FIG. 23 depicts the oligo-NIPAm-12i-4s-12i composition which demonstrates two well-separated conformational states, unfolded (2300) and folded (2301) ones, with reproducible reversible transitions between the stretched form and the L-shaped lever-like form in response to external stimulus. In FIG. 23, element (2803) depicts a bending or hinge subcomponent, and elements (2302) depict rigid subcomponents.

Figure 24:
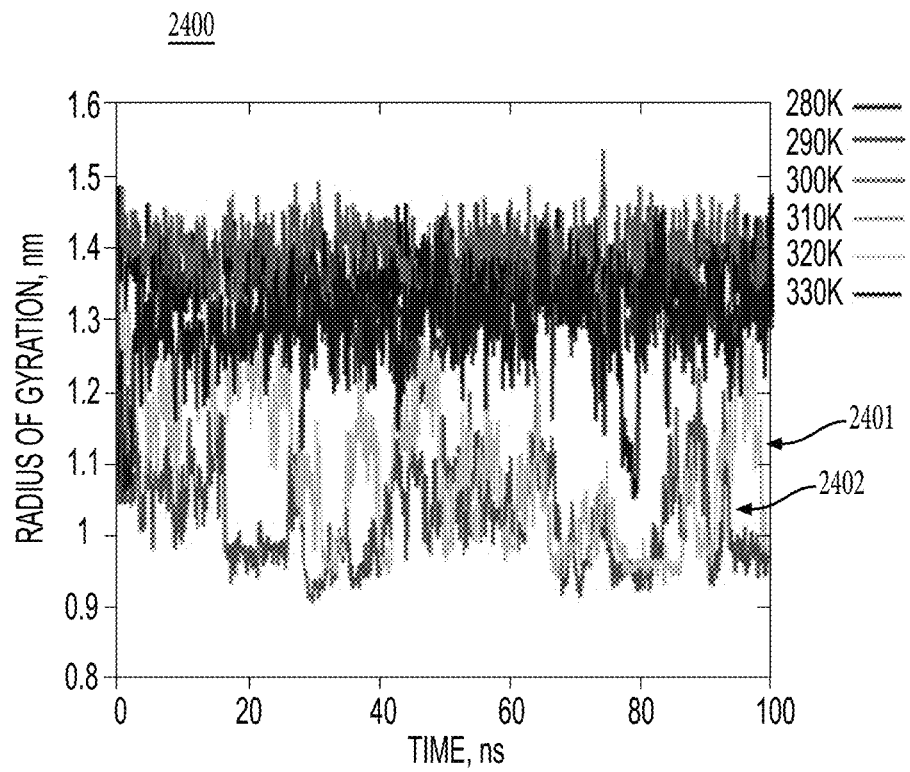
FIG. 24 depicts radius of gyration vs simulation time for an exemplary 12i-6s-12i NIPAm tri-block embodiment.
Figure 25:
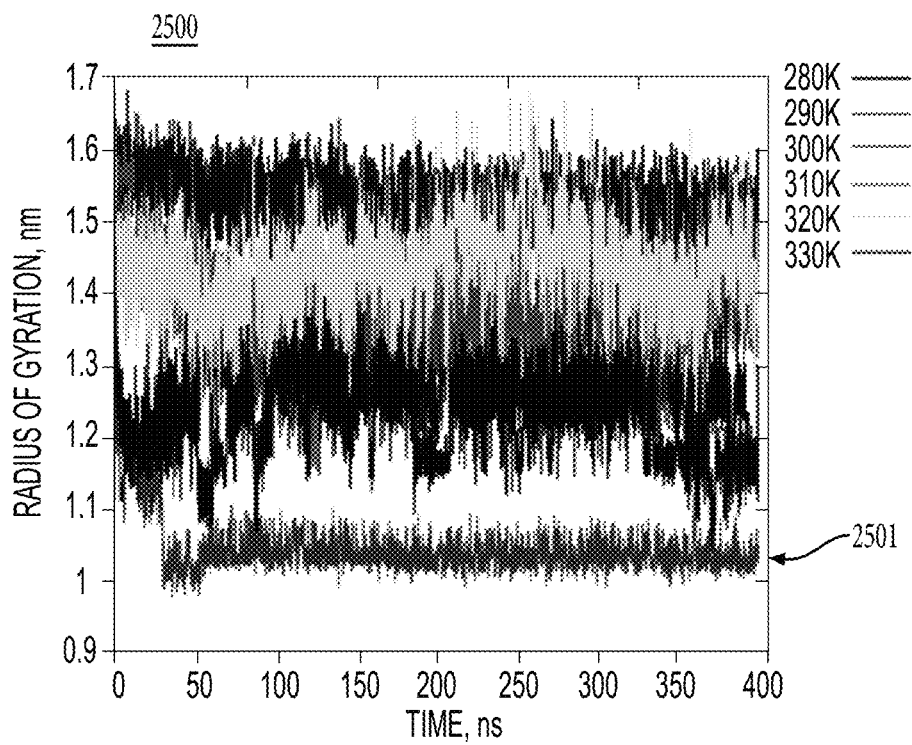
FIG. 25 depicts radius of gyration vs simulation time for an exemplary oligo-NIPAm-12i-8s-12i tri-block embodiment.
Figure 26:
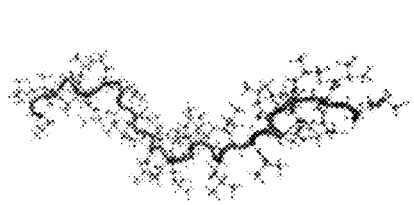
FIG. 26 depicts unfolded (3100), folded (3101), and semi-folded (3102) states of an exemplary NIPAm-12i-8s-12i tri-block embodiment.
Figure 26:
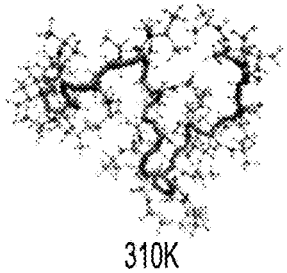
Figure 26:
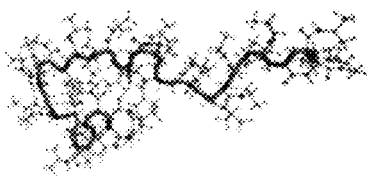
Figure 27:
FIG. 27 depicts unfolded (3200) and folded (3201) shapes of an exemplary oligo-NIPMAm-12i-7s-12i tri-block embodiment.
Figure 27:
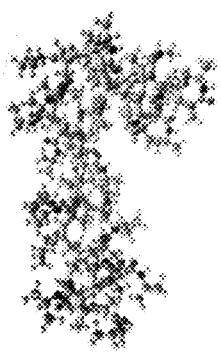

In another exemplary embodiment, a three-block oligomeric machine consists of two edge blocks, each of 15 NIPAm monomers connected isotactically are joined by a bending or hinge location composed of 10 NIPAm monomers connected syndiotactically and is named oligo-NIPAm-15i-10s-15i. Below LCST the composition exists as a stretched rod-like structure with an average gyration radius of 1.5 nm, while above the LCST it folds into a V-shaped hairpin-like form with an average radius of gyration of 1.25 nm. FIG. 24 depicts unfolded and folded shapes of oligo-NIPAm-15i-10s-15i three-block oligomeric machine. The oligo-NIPAm-15i-10s-15i composition also demonstrates two well-separated conformational states, unfolded and folded ones, with reproducible reversible transitions between the rod-like stretched form and the V-shaped hairpin-like form in response to external stimulus. Results of full atomic computer simulation of three oligo-NIPAm-compositions 12s-8i-12s, 9i-6s-9i and 12i-6s-12i are depicted in FIG. 25. Changing the order of blocks (that is, switching from 12i-8s-12i to 12s-8i-12s) leads to absence of bistability wherein the system has the same conformational state with an average radius of gyration of 1.25 nm at 290K and at 320K. Relatively short isotactic blocks (in 9i-6s-9i oligomer) seem to be less stiff due to lower probability of forming hydrogen bonds along the chain that sharply reduces the persistent length. As a result, the oligomeric machine folds to both 290K and 320K with an average gyration radius of 1 nm. Oligomeric machine named 12i-6s-12i shows different conformational states at temperatures below and above LCST, and the folded state strongly fluctuates. In some exemplary embodiments, other choices of three-block compositions may have two conformational states, but may exhibit less controllability in changes of mutual orientations of rigid edges of the chain when it folds in response to external stimulus. Such an exemplary embodiment may be a three-block oligomeric machine consisting of two edge blocks, each of 12 NIPAm monomers connected isotactically, which are joined by a bending location composed of 8 NIPAm monomers connected syndiotactically. This exemplary embodiment is named oligo-NIPAm-12i-8s-12i. FIG. 26 depicts a series of simulations at different temperatures with a step of 10K. At 280K the structure behaves as a stiff rod (2600). At 310K it collapses into well-folded S-shape state (2601). At 330K, due to high temperature, the entropy dominates over the hydrophobic interactions making the folded S-shape unstable (2602). Note that the composition's shape is unchanged over large simulation time. In some embodiments, additional three-block oligomers of NIPMAm are demonstrated. Isotactic fragments demonstrating high stiffness may be used as edge blocks, and syndiotactic fragments may bend and a syndiotactic fragment may be incorporated as a bending or hinge location. A preferred three-block oligomer comprising two edge blocks, each of 12 NIPMAm monomers connected isotactically may be joined by the bending location composed of 7 NIPMAm monomers connected syndiotactically and this exemplary embodiment is denoted by oligo-NIPMAm-12i-7s-12i. This oligomeric machine possesses conformational bistability with a critical temperature close to 300 K. Below the critical temperature it exists as a stretched rod-like structure with an average gyration radius of 1.26 nm, while above the critical temperature it folds into a Γ-shaped lever-like conformation with an average radius of gyration of 1.12 nm. As FIG. 27 depicts, an oligo-NIPMAm-12i-7s-12i composition demonstrates two well-separated conformational states, unfolded (2700) and folded (2701) ones, with reproducible reversible transitions between the stretched form and the Γ-shaped lever-like form in response to external stimulus.

Figure 28A:
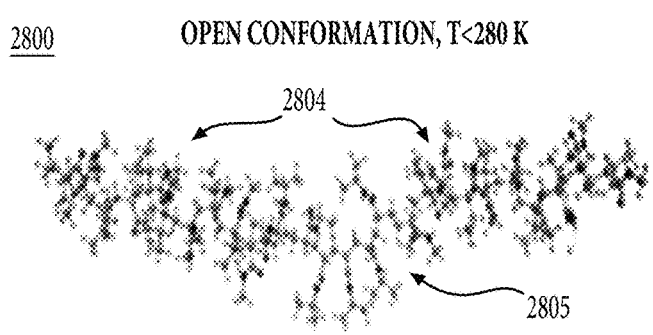
FIG. 28A depicts an exemplary 10-7-10-NMIPAm-NIPMAm-NMIPAm chimeric composition in an open conformation.
Figure 28B:
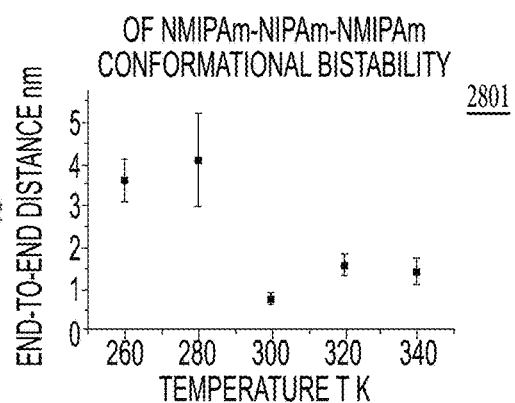
FIG. 28B depicts end-to-end distance vs temperature of an exemplary embodiment.
Figure 28C:
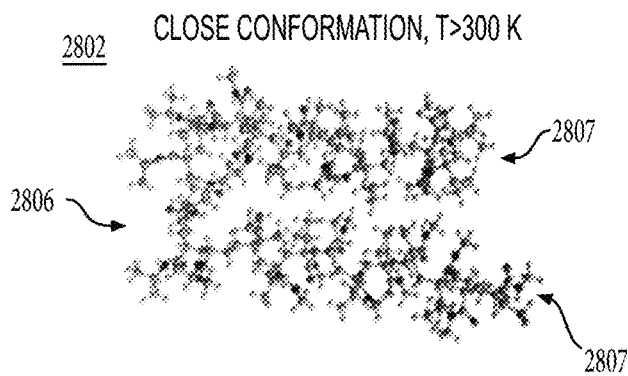
FIG. 28C depicts an exemplary 10-7-10-NMIPAm-NIPMAm-NMIPAm chimeric composition in a closed conformation.
Figure 28D:
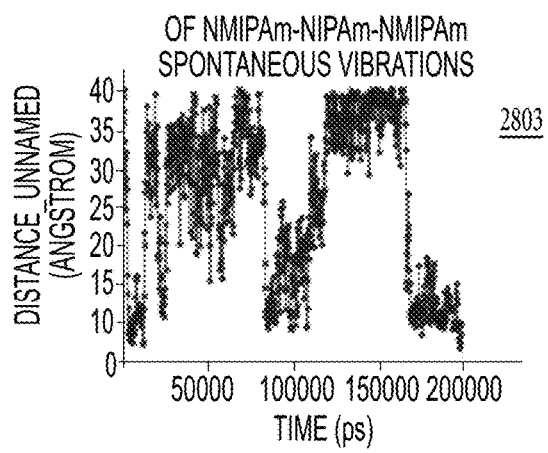
FIG. 28D depicts spontaneous vibrations of an exemplary embodiment at T=320K.

In another embodiment, three-block co-oligomers comprising two rigid blocks are joined by a bending third block. In some embodiments, oligo-NMIPAm fragments, a stereoisomer of NIPAm which methyl and isopropyl groups are replaced one by another, demonstrate high rigidity, and can be used as rigid edge blocks in the composition while oligo-NIPAm fragments may bend, and may be positioned at a bending or hinge location. For instance, a preferred three-block chimeric oligomer may comprise two edge NMIPMAm-blocks each of 10 monomers and are joined by the bending location composed of 7 NIPMAm monomers of isotactic configuration. The composition of this embodiment is denoted 10-7-10-NMIPMA-NIPMA-NMIPMA. In FIGS. 28A and C, elements (2805 and 2806) depict a bending or hinge subcomponent, and elements (2804 and 2807) depict rigid subcomponents. FIG. 28A (2800) depicts an open conformation for this embodiment. FIG. 28C (2802) depicts a close conformation for this embodiment. FIG. 28B (2801) depicts the conformational bistability exhibited by this embodiment FIG. 28D (2803) depicts spontaneous vibrations exhibited by this embodiment at 320 K. This chimeric embodiment possesses a conformational transition above 300 K. Below the critical temperature it exists as an "open", stretched structure with an average end-to-end distance about of 4 nm, while above the critical temperature it folds in half in to the "closed" conformation with the end-to-end distance about of 1 nm in average. Near the critical temperature, the 10-7-10-NMIPMA-NIPMA-NMIPMA composition demonstrates spontaneous transitions between the open and closed states, thus reproducibly changing mutual orientation of the rigid NMIPMAm fragments in response to external stimuli. A series of computational experiments were conducted on this embodiment. Full atomic GROMACS molecular dynamics package were used to perform atomistic simulations of NMIPMA-NIPMA-NMIPMA oligomers in water solution at temperatures ranged from 290K to 360K. OPLS-AA force field in combination with TIP3P explicit water model are used to describe inter- and intra-molecular interactions. The conformation of the chain is characterized by its radius of gyration and the distance between the oligomer ends.

In some exemplary embodiments, two joined oligomeric modules possess conformational bistability with controlled conformational change. The molecular and/or oligomeric machine component comprises a first oligomeric module having a first end and a second end and a second oligomeric module having a first end and a second end. The first end of the first oligomeric module is joined to the first end of the second oligomeric module to form an oligomeric chain, and the second end of the first oligomeric module is disconnected from the second end of the second oligomeric modules. The first oligomeric module and the second oligomeric module are selected and joined so that a pair of joined oligomeric modules possesses conformational bistability. A relative orientation of the first oligomeric module and the second oligomeric module spontaneously changes from a first orientation to a second orientation above a critical temperature. The relative orientation of the first oligomeric module and the second oligomeric module repeatedly changes from a first orientation to a second orientation in response to energy applied to the joined oligomeric modules. An oligomeric module may have a length between 0.5 nm and 20 nm. The relative orientation of the first and second oligomeric modules may define a conformation, and two such stable or metastable conformations may exist. A transition between a first conformation and a second conformation may include relative motion of the first and second oligomeric modules. An oligomeric module may comprise at least 5 repeat units. An oligomeric module may comprise at least 10 repeat units. An oligomeric module may comprise at least 15 repeat units. An oligomeric module may comprise at least 20 repeat units. An oligomeric module may comprise at least 25 repeat units. An oligomeric module may comprise at least 30 repeat units. An oligomeric module may comprise poly-N-isopropylacrylamide. An oligomeric module may comprise poly-N-isopropylmethacrylamide. An oligomeric and/or molecular machine component may be configured so as to exhibit a conformational transitional point within 250 K to 400 K. An oligomeric and/or molecular machine component may be configured so as to exhibit a conformational transitional point within 275 K to 375 K. An oligomeric and/or molecular machine component may be configured so as to exhibit a conformational transitional point within 300 K to 350 K. An oligomeric module may comprise a single type of monomeric unit. An oligomeric module may comprise NIPAm residues.

In some exemplary embodiments, oligomeric machines may include Poly(N-isopropylacrylamide). A synthetic oligomer for a bistable oligomeric machine may comprise a fragment of Poly(N-isopropylacrylamide) (PNIPAm) of at least 15 repeating units. The PNIPAm-oligomer may be stereo-regular or stereo-irregular. The PNIPAm-oligomer may comprise regions which are isotactic, syndiotactic, and/or atactic. The PNIPAm oligomer may be such that at least a one-third portion of the PNIPAm oligomer does not flex more than 50% along a length of the at least one-third portion. The PNIPAm-oligomer may have conformational bistability with reproducible change of mutual displacement of the oligomer fragment ends above a critical temperature. The PNIPAm-oligomer may exhibit thermally activated stochastic resonance with reproducible change of mutual displacement of the oligomer fragment ends above a critical temperature. The PNIPAm-oligomer may be a block-co-oligomer. A block-co-oligomer may be composed of certain portions, each in isotactic, syndiotactic, or atactic form. A PNIPAm-co-oligomer may be selected such that each block of the PNIPAm-co-oligomer composition does not flex more than 50% along a length of the block. The oligomer may comprise 20 units of NIPAm. The oligomer may comprise 25 units of NIPAm. The oligomer may comprise 30 units of NIPAm.

In some exemplary embodiments, oligomeric machines may include Poly (N-isopropylmethacrylamide). A synthetic oligomer for an oligomeric machine may comprise a fragment of Poly(N-isopropylmethacrylamide) (PNIPMAm) of at least 15 repeating units. The PNIPMAm-oligomer may be stereo-regular or stereo-irregular. The PNIPMAm-oligomer may comprise regions which are isotactic, syndiotactic, and/or atactic. The PNIPMAm oligomer may be such that at least a one-third portion of the PNIPMAm oligomer does not flex more than 50% along a length of the at least one-third portion. The PNIPMAm-oligomer may have conformational bistability with reproducible change of mutual displacement of the oligomer fragment ends above a critical temperature. The PNIPMAm-oligomer may exhibit thermally activated stochastic resonance with reproducible change of mutual displacement of the oligomer fragment ends above a critical temperature. The PNIPMAm-oligomer may be a block-co-oligomer. A block-co-oligomer may be composed of certain portions, each in isotactic, syndiotactic, or atactic form. A PNIPMAm-co-oligomer may be selected such that each block of the PNIPMAm-co-oligomer composition does not flex more than 50% along a length of the block. The PNIPMAm-co-oligomer may have conformational bistability with reproducible change of mutual arrangement of the blocks above a critical temperature. The oligomer may comprise 20 units of NIPMAm. The oligomer may comprise 25 units of NIPMAm. The oligomer may comprise 30 units of NIPMAm.

Some exemplary embodiments may include chimeric bistable oligomeric machines. A synthetic oligomer for a molecular and/or oligomeric machine may comprise a fragment of Poly(N-isopropylacrylamide) (PNIPAm) of at least 5 repeating units in the stereo-regular or the stereo-irregular form and at least one other oligomeric fraction other than PNIPAm of at least 0.5 nm in length and/or possessing a persistence length of at least 0.5 nm. At least one portion of the PNIPAm may be such that it does not flex more than 50% along a length of the at least one portion of the PNIPAm oligomer and does not flex more than 50% along a length of the at least one-third portion. The oligomer fragment may exhibit stochastic resonance with reproducible change of spatial arrangements of the fragment ends above a critical temperature. The oligomer composition may include three oligomeric modules with two edge NMIPAm-modules each of 10 monomers which are joined by a bending location composed of 7 NIPMAm monomers of isotactic configuration. A chimeric composition may allow for significant customization of the structure and function of a molecular and/or oligomeric machine such as, for example, length, rigidity, and/or chemical functionalization. The oligomer composition may comprise three modules with two edge NMIPAm-modules each of 8 monomers, which are joint by the bending location composed of 5 NIPMAm monomers of isotactic configuration.

Additional exemplary embodiments may include oligomeric machines configured for mechanical force generation.

A molecular and/or oligomeric machine may comprise a synthetic material including a first oligomeric module and a second oligomeric module joined to the first oligomeric module to form an oligomeric chain, at least one bending or hinge location at a position of co-joinder between the first oligomeric module and the second oligomeric module, the bending or hinge location permitting relative flexure between the first oligomeric module and the second oligomeric module, at least one element of a piston type; and a substrate configured with the piston element and the oligomeric chain such that the second oligomeric module of the oligomeric chain is capable of mechanically actuating the piston element. The piston element may be any suitable rigid molecular and/or nanoscale structure such as for instance a graphene nanotube, a nano-wire, and/or a DNA fragment. A bistable oligomer machine may generate mechanical force by transmitting the movements of a bistable oligomer machine to cyclic movement of a piston type element.

Another non-limiting exemplary embodiment may include bistable oligomeric machines for electro-mechanical nano-devices. A molecular and/or oligomeric machine may comprise a synthetic material including a first oligomeric module and a second oligomeric module joined to the first oligomeric module to form an oligomeric chain, at least one bending or hinge location at a position of co-joinder between the first oligomeric module and the second oligomeric module, the bending or hinge location permitting relative flexure between the first oligomeric module and the second oligomeric module; at least one electric generating element, and a substrate configured with the electric generating element and the oligomeric chain such that the second oligomeric module of the oligomeric chain is capable of mechanically actuating the electric generating elements. The oligomeric chain may be formed such that in response to a prescribed amount of energy applied thereto, relative movement occurs between the first oligomeric module and the second oligomeric module in a manner causing the mechanical action of the second oligomeric module on the electric generating element to produce an electrical voltage and/or current. The electric generating element may be a piezoelectric element, a nano-particle, a nano-wire, and/or a nano-layer. A molecular and/or oligomeric machine may be configured to generate a voltage by performing a mechanical action on a piezoelectric element.

Other exemplary embodiments may include bistable oligomeric machines for energy harvesting.

A molecular and/or oligomeric machine may comprise a synthetic material including a first oligomeric module and a second oligomeric module joined to the first oligomeric module to form an oligomeric chain, at least one bending or hinge location at a position of co joinder between the first oligomeric module and the second oligomeric module, the bending or hinge location permitting relative flexure between the first oligomeric module and the second oligomeric module; at least one light-absorbing element attached to the oligomeric chain at the bending or hinge location, at least one electric generating element, and a substrate configured with the electric generating element and the oligomeric chain such that the second oligomeric modules of the oligomeric chain to ensure the mechanical action on the electric generating elements. The oligomeric chain may be formed such that in response to a prescribed amount of energy applied thereto, relative movement occurs between the first oligomeric module and the second oligomeric module in a manner causing the mechanical action of the second oligomeric module on the electric generating element to produce an electrical voltage and/or current. The electric generating element may be a piezoelectric element, a nano-particle, a nano-wire, and/or a nano-layer. A molecular and/or oligomeric machine may be configured to generate a voltage by performing a mechanical action on a piezoelectric element. A light absorbing element may be a dye, a compound comprising aromatic groups, a compound comprising conjugation, and/or a semi-conducting element.

Additional Non-Limiting Exemplary Embodiments Include

In some embodiments, an oligomeric machine comprises a first oligomeric module having a first end and a second end, and a second oligomeric module having a first end and a second end; wherein the first end of the first oligomeric module is joined to the first end of the second oligomeric module; and wherein the oligomeric machine exhibits stochastic resonance in a solution at a temperature when the temperature is in a critical temperature range and the oligomeric machine does not exhibit stochastic resonance in the solution when the temperature is not in the critical temperature range.

In some embodiments, an oligomeric machine comprises a first oligomeric module having a first end and a second end, and a second oligomeric module having a first end and a second end; wherein the first end of the first oligomeric module is joined to the first end of the second oligomeric module; and wherein the oligomeric machine exhibits spontaneous vibrations in a solution at a temperature when the temperature is in a critical temperature range and the oligomeric machine does not exhibit spontaneous vibrations in the solution when the temperature is not in the critical temperature range.

In some embodiments, an oligomeric machine comprises a first oligomeric module having a first end and a second end, and a second oligomeric module having a first end and a second end; wherein the first end of the first oligomeric module is joined to the first end of the second oligomeric module; wherein the oligomeric machine exhibits spontaneous vibrations in a solution at a temperature when the temperature is in a critical temperature range and the oligomeric machine does not exhibit spontaneous vibrations in the solution when the temperature is not in the critical temperature range; wherein the spontaneous vibrations have a non-regular frequency.

In some embodiments, an oligomeric machine comprises a first oligomeric module having a first end and a second end, and a second oligomeric module having a first end and a second end; wherein the first end of the first oligomeric module is joined to the first end of the second oligomeric module; wherein the oligomeric machine exhibits spontaneous vibrations in a solution at a temperature when the temperature is in a critical temperature range and the oligomeric machine does not exhibit spontaneous vibrations in the solution when the temperature is not in the critical temperature range; wherein the spontaneous vibrations have a non-regular frequency; and wherein, upon application of a oscillatory force having a force load within a critical force range and a force frequency to the oligomeric machine when the temperature is in the critical range, the oligomeric machine exhibits stochastic resonance having a frequency substantially the same as the force frequency.

In some embodiments, an oligomeric machine comprises a first oligomeric module having a first end and a second end, and a second oligomeric module having a first end and a second end; wherein the first end of the first oligomeric module is joined to the first end of the second oligomeric module; and wherein the oligomeric machine exhibits stochastic resonance in a solution at a temperature when the temperature is in a critical temperature range and the oligomeric machine does not exhibit stochastic resonance in the solution when the temperature is not in the critical temperature range.

In some embodiments, an oligomeric machine comprises a first oligomeric module having a first end and a second end, and a second oligomeric module having a first end and a second end; wherein the first end of the first oligomeric module is joined to the first end of the second oligomeric module; and wherein the oligomeric machine exhibits spontaneous vibrations in a solution under a force load applied to the oligomeric machine when the force load is in a critical force range while the temperature is not in a critical temperature range, and the oligomeric machine does not exhibit spontaneous vibrations in the solution when the force load and the temperature are not in the critical ranges.

In some embodiments, an oligomeric machine comprises a first oligomeric module having a first end and a second end, and a second oligomeric module having a first end and a second end; wherein the first end of the first oligomeric module is joined to the first end of the second oligomeric module; and wherein the oligomeric machine exhibits stochastic resonance in a solution under a force load applied to the oligomeric machine when the force load is in a critical force range while the temperature is not in a critical temperature range, and the oligomeric machine does not exhibit stochastic resonance in the solution when the force load and the temperature are not in the critical ranges.

In some embodiments, the oligomeric machine further comprises at least one bending or hinge location at a position of co-joinder between the first oligomeric module and the second oligomeric module, the bending or hinge location permitting relative flexure between the first oligomeric module and the second oligomeric module.

In some embodiments, the first and/or second oligomeric module comprises optionally substitute acrylamide residues, optionally substituted (meth)acrylamide residues, optionally substituted (meth)acrylic acid residues, optionally substituted aziridine residues, optionally substituted epoxy residues, alkoxy substituted ethane residues, or combinations thereof.

In some embodiments, the first and/or second oligomeric module comprises at least one of N-ethylacrylamide residues, 2-(isopropylcarbamoyl)acrylic acid residues, 1-(aziridin-1-yl)-2-methylpropan-1-one residues, methoxyethene residues, and 2-methyloxirane residues.

In some embodiments, the first end of the first oligomeric module is joined to the first end of the second oligomeric module through a linker unit having a persistence length that is less than the persistence length of both the first and second oligomeric modules.

In some embodiments, the first and second oligomeric modules each comprise from 10 to 30 repeat units.

In some embodiments, the first and second oligomeric modules each comprise from 10 to 30 stereo-regular repeat units.

In some embodiments, the first and second oligomeric modules each have a persistence length from 0.5 nm to 20 nm.

In some embodiments, the solution is an aqueous solution.

In some embodiments, the critical temperature range is within the temperature range given by −25° C. to 100° C.

In some embodiments, the critical temperature range is within the temperature range given by 25° C. to 45° C.

In some embodiments, the critical force range is within the force range given by 10 pN (pico-Newton) to 1000 pN.

In some embodiments, the critical force range is within the force range given by 250 pN (pico-Newton) to 350 pN.

In some embodiments, the critical force range is within the force range given by 375 pN (pico-Newton) to 400 pN.

In some embodiments, an oligomeric machine component configured to exhibit conformational bistability, comprises a first oligomeric module having a first end and a second end and a second oligomeric module having a first end and a second end; wherein the first end of the first oligomeric module is joined to the first end of the second oligomeric module; and wherein a relative orientation of the first oligomeric module and the second oligomeric module changes from a first orientation to a second orientation in response to an applied stimulus.

In some embodiments, the oligomeric machine component repeatedly fluctuates between the first orientation and second orientation in response to the applied stimulus.

In some embodiments, an applied stimulus is a first stimulus and the relative orientation of the first oligomeric module and the second oligomeric module changes from the second orientation to the first orientation upon application of an additional stimulus and/or cessation of the first stimulus.

In some embodiments, the applied stimulus is any one or more of a change in temperature, a set temperature, an electric field, a magnetic field, a change in pH, an applied force of at least 10 picoNewtons, a prescribed amount of energy, and/or a change in ionic strength.

In some embodiments, the oligomeric machine component further comprises at least one bending or hinge location at a position of co-joinder between the first and second oligomeric modules.

In some embodiments, the at least one bending or hinge location comprises a third oligomeric module having a flexibility substantially greater than the flexibility of each of the first and second oligomeric modules.

In some embodiments, the applied stimulus causes the third oligomeric module to flex while the first and second oligomeric modules remains substantially un-flexed.

In some embodiments, the oligomeric machine component further comprises at least one extender formed of a material different from the first and second oligomeric modules and having a flexibility less than the flexibility of the oligomeric modules.

In some embodiments, each oligomeric segment has a length from 0.5 nm up to 15 nm.

In some embodiments, at least one oligomeric module comprises at least 15 repeating units of stereo-regular or stereo-irregular Poly(N-isopropylacrylamide).

In some embodiments, at least one oligomeric module comprises at least 15 repeating units of stereo-regular or stereo-irregular Poly(N-isopropylmethacrylamide).

In some embodiments, the first oligomeric module comprises at least 5 repeating units of Poly(N-isopropylacrylamide) in the stereo-regular or the stereo-irregular form, the second oligomeric module does not comprise Poly(N-isopropylacrylamide) and has a persistence length of at least 0.5 nm, and at least a one-third portion of the first oligomeric module does not flex more than 50% along a length of the at least one-third portion.

In some embodiments, at least one of the first or second oligomeric modules comprises an isotactic block.

In some embodiments, at least one of the first or second oligomeric modules comprises an atactic block.

In some embodiments, at least one of the first or second oligomeric modules comprises a syndiotactic block.

In some embodiments, the first and second oligomeric modules are selected and joined such that the oligomeric machine component is configured to have a conformational transitional temperature within 250 K to 400 K.

In some embodiments, the first and second oligomeric modules comprise a common monomeric unit.

In some embodiments, the oligomeric machine component further comprises a rigid molecular structure such as a nanotube or DNA.

In some embodiments, the joined first and second oligomeric modules comprises an isotactic Poly(N-isopropylacrylamide) block and an atactic Poly(N-isopropylacrylamide) block.

In some embodiments, the joined first and second oligomeric modules comprises a Poly(N-isopropylmethacrylamide) block between two Poly(2-Isopropyl-N-methylacrylamide) blocks.

In some embodiments, an oligomeric machine, comprises a synthetic material including a first oligomeric module and a second oligomeric module joined to the first oligomeric module to form an oligomeric chain; at least one bending or hinge location at a position of co-joinder between the first oligomeric module and the second oligomeric module, the bending or hinge location permitting relative flexure between the first oligomeric module and the second oligomeric module; at least one electric generating element; a substrate configured relative to the at least one electric generating element and the oligomeric chain such that the relative flexure between the first oligomeric module and the second oligomeric module results in mechanical interaction between at least the second oligomeric module of the oligomeric chain and the at least one electric generating element; and wherein the oligomeric chain is formed such that in response to a stimulus, the relative flexure occurs between the first oligomeric module and the second oligomeric module in a manner causing the mechanical interaction between the second oligomeric module and the electric generating element, and wherein the mechanical interaction produces a change in electrical voltage associated with the at least one electric generating element.

In some embodiments, the oligomeric machine further comprises at least one light-absorbing element attached to the oligomeric chain at the at least one bending or hinge location wherein the oligomeric chain with light-absorbing element is formed such that in response to a prescribed amount of light energy applied to the light-absorbing element, the relative flexure occurs between the first oligomeric module and the second oligomeric module in a manner causing the mechanical interaction between the second oligomeric module and the at least one electric generating element to produce a change in electrical voltage associated with the at least one electric generating element.

In some embodiments, the electric generating element includes at least one of a piezoelectric element, nano-particle, nano-wire, or nano-layer.

In some embodiments, an oligomeric machine, comprises a synthetic material including a first oligomeric module and a second oligomeric module joined to the first oligomeric module to form an oligomeric chain; at least one bending or hinge location at a position of co-joinder between the first oligomeric module and the second oligomeric module, the bending or hinge location permitting relative flexure between the first oligomeric module and the second oligomeric module; at least one piston element; a substrate configured relative to the at least one piston element and the oligomeric chain such that the relative flexure between the first oligomeric module and the second oligomeric module results in mechanical interaction between at least the second oligomeric module of the oligomeric chain and the at least one piston element; and wherein the oligomeric chain is formed such that in response to a prescribed amount of energy applied thereto, the relative flexure occurs between the first oligomeric module and the second oligomeric module in a manner causing the mechanical interaction between the second oligomeric module and the piston element, and wherein the mechanical interaction produces a mechanical force.

In some embodiments, the piston element is at least one of a graphene nanotube, a nano-wire, or a DNA fragment.

In some embodiments, the oligomeric chain comprises a Poly(N-isopropylmethacrylamide) block between two Poly(2-Isopropyl-N-methylacrylamide) blocks.

Unless otherwise defined, all technical and scientific terms used herein have the same meaning as commonly understood by one of ordinary skill in the art. In case of conflict, the present document, including definitions, will control. Preferred methods and materials are described herein, although methods and materials similar or equivalent to those described herein can be used in practice or testing of embodiments of the present disclosure. The materials, methods, and examples disclosed herein are illustrative only and not intended to be limiting. The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an," and "the" include plural references unless the context clearly dictates otherwise. The present disclosure also contemplates other embodiments "comprising," "consisting of," and "consisting essentially of" the embodiments or elements presented herein, whether explicitly set forth or not. The conjunctive term "or" may include any and all combinations of one or more listed elements associated by the conjunctive term. For example, the phrase "an apparatus comprising a or b" may refer to an apparatus including a where b may be not present, an apparatus including b where a may be not present, or an apparatus where both a and b are present. The phrases "at least one of a, b, . . . , and n" or "at least one of a, b, . . . , n, or combinations thereof" are defined in the broadest sense to mean one or more elements selected from the group comprising a, b, . . . , and n, that is to say, any combination of one or more of the elements a, b, . . . , or n including any one element alone or in combination with one or more of the other elements, which may also include, in combination, additional elements not listed. The terms "first," "second," "third," and the like, as used herein, do not denote any order, quantity, or importance, but rather are used to distinguish one element from another. The term "substantially," as used herein, represents the inherent degree of uncertainty that may be attributed to any quantitative comparison, value, measurement, or other representation. The term "substantially" may be also utilized herein to represent the degree by which a quantitative representation may vary from a stated reference without resulting in a change in the basic function of the subject matter at issue. The term "at least one bending location or one hinge location" refers to at least one position of co-joinder between the at least two oligomeric modules that allow the at least two oligomeric modules to predictably flex relative to each other about the bending or hinge location.

What is claimed is:

1. An oligomeric machine for energy harvesting comprising:

a first oligomeric module having a first end and a second end,
    a second oligomeric module having a first end and a second end, and
    at least one electric generating element;
    wherein the first end of the first oligomeric module is joined to the first end of the second oligomeric module; and
    wherein the oligomeric machine is configured such that in response to a prescribed amount of energy applied thereto, relative movement occurs between the first oligomeric module and the second oligomeric module in a manner causing the mechanical action of the second oligomeric module on the at least one electric generating element to produce an electrical voltage and/or current; and
    wherein the oligomeric machine exhibits stochastic resonance and/or spontaneous vibrations in a solution at a temperature when the temperature is in a critical temperature range and the oligomeric machine does not exhibit stochastic resonance and/or spontaneous vibrations in the solution when the temperature is not in the critical temperature range; and
    wherein the oligomeric machine exhibits stochastic resonance and/or spontaneous vibrations in a solution under a force load applied to the oligomeric machine when the force load is in a critical force range and the oligomeric machine does not exhibit stochastic resonance and/or spontaneous vibrations in the solution when the force load is not in the critical force range.

2. The oligomeric machine according to claim 1, further comprising at least one bending or hinge location at a position of co joinder between the first oligomeric module and the second oligomeric module, the bending or hinge location permitting relative flexure between the first oligomeric module and the second oligomeric module.

3. The oligomeric machine according to claim 1, wherein the first and/or second oligomeric module comprises optionally substitute acrylamide residues, optionally substituted (meth)acrylamide residues, optionally substituted (meth)acrylic acid residues, optionally substituted aziridine residues, optionally substituted epoxy residues, alkoxy substituted ethane residues, or combinations thereof.

4. The oligomeric machine according to claim 1, wherein the first and/or second oligomeric module comprises at least one of N-ethylacrylamide residues, 2-(isopropylcarbamoyl) acrylic acid residues, 1-(aziridin-1-yl)-2-methylpropan-1-one residues, methoxyethene residues, and 2-methyloxirane residues.

5. The oligomeric machine according to claim 1, wherein the first end of the first oligomeric module is joined to the first end of the second oligomeric module through a linker unit having a persistence length that is less than the persistence length of both the first and second oligomeric modules.

6. The oligomeric machine according to claim 1, wherein the first and second oligomeric modules each comprise from 10 to 30 repeat units.

7. The oligomeric machine according to claim 1, wherein the first and second oligomeric modules each comprise from 10 to 30 stereo-regular repeat units.

8. The oligomeric machine according to claim 1, wherein the first and second oligomeric modules each have a persistence length from 0.5 nm to 20 nm.

9. The oligomeric machine according to claim 1, wherein the solution is an aqueous solution.

10. The oligomeric machine according to claim 1, wherein the critical temperature range is within the temperature range given by −25° C. to 100° C.

11. The oligomeric machine according to claim 1, wherein the critical temperature range is within the temperature range given by 25° C. to 45° C.

12. The oligomeric machine according to claim 1, wherein the critical force range is within the force range given by 10 pN to 1000 pN.

13. The oligomeric machine according to claim 1, wherein the critical force range is within the force range given by 250 pN to 350 pN.

14. The oligomeric machine according to claim 1, wherein the critical force range is within the force range given by 350 pN to 400 pN.

15. The oligomeric machine according to claim 1, wherein the at least one electric generating element is chosen from a piezoelectric element, a nano-particle, a nano-wire, and a nano-layer.

16. The oligomeric machine according to claim 1, wherein the oligomeric machine is configured to generate a voltage by performing a mechanical action on a piezoelectric element.

* * * * *